US007022674B2

(12) United States Patent
DeFelippis et al.

(10) Patent No.: US 7,022,674 B2
(45) Date of Patent: Apr. 4, 2006

(54) POLYPEPTIDE COMPOSITIONS WITH IMPROVED STABILITY

(75) Inventors: Michael Rosario DeFelippis, Carmel, IN (US); Michael Allen Dobbins, Lebanon, IN (US); Alby David Sharknas, Indianapolis, IN (US); Alex Mark Prokai, Carmel, IN (US); Joseph Vincent Rinella, Ypsilanti, MI (US)

(73) Assignee: Eli Lilly and Company, Indianapolis, IN (US)

( * ) Notice: Subject to any disclaimer, the term of this patent is extended or adjusted under 35 U.S.C. 154(b) by 509 days.

(21) Appl. No.: 10/130,836

(22) PCT Filed: Dec. 5, 2000

(86) PCT No.: PCT/US00/32421

§ 371 (c)(1),
(2), (4) Date: May 21, 2002

(87) PCT Pub. No.: WO01/43762

PCT Pub. Date: Jun. 21, 2001

(65) Prior Publication Data

US 2003/0207802 A1    Nov. 6, 2003

Related U.S. Application Data

(60) Provisional application No. 60/181,030, filed on Feb. 8, 2000, provisional application No. 60/171,135, filed on Dec. 16, 1999.

(51) Int. Cl.
*A61K 38/00* (2006.01)

(52) U.S. Cl. .......................... 514/12; 514/3

(58) Field of Classification Search ................ 514/12, 514/21, 1; 424/455
See application file for complete search history.

(56) References Cited

U.S. PATENT DOCUMENTS

| 4,076,758 | A |   | 2/1978  | Owsley et al. |       |
|-----------|---|---|---------|---------------|-------|
| 4,683,347 | A |   | 7/1987  | Diaz et al.   |       |
| 5,124,314 | A |   | 6/1992  | Cooper        |       |
| 5,164,366 | A |   | 11/1992 | Balschmidt et al. |   |
| 5,514,646 | A |   | 5/1996  | Chance et al. |       |
| 5,618,913 | A |   | 4/1997  | Brange et al. |       |
| 5,750,166 | A |   | 5/1998  | Schellhaass   |       |
| 5,951,993 | A |   | 9/1999  | Scholz et al. |       |
| 5,969,175 | A |   | 10/1999 | Murao et al.  |       |
| 6,034,054 | A | * | 3/2000  | DeFelippis et al. | 514/4 |
| 6,136,784 | A |   | 10/2000 | L'italien et al. |    |
| 6,268,343 | B1| * | 7/2001  | Knudsen et al. | 514/12 |
| 6,358,924 | B1| * | 3/2002  | Hoffmann      | 514/12 |
| 6,551,992 | B1| * | 4/2003  | DeFelippis et al. | 514/3 |

FOREIGN PATENT DOCUMENTS

| CA | 2242591       | 7/1998  |
|----|---------------|---------|
| DK | 173015 B1     | 6/1996  |
| EP | 0 849 276 A1  | 12/1997 |
| EP | 0 885 961 A1  | 6/1998  |
| WO | WO 97/48414   | 12/1997 |
| WO | WO 98/21340   | 5/1998  |
| WO | WO 99/28480   | 6/1999  |
| WO | WO 99/29336   | 6/1999  |
| WO | WO 99/29337   | 6/1999  |
| WO | WO 99/43708   | 9/1999  |
| WO | WO 00/07617   | 2/2000  |
| WO | WO 00/38652   | 7/2000  |
| WO | WO 00/41546   | 7/2000  |

OTHER PUBLICATIONS

Peter Klusmann, Novo Nordisk, Grounds for Appeal filed with the German Federal Patent Court Against the German Patent Office in Proceedings relating to the German Utility Model that Corresponds to this U.S. Appl. No. 10/130,836, filed Dec. 17, 2004.*
Rohde, T.D., et al., "An Improved Glycerol/Insulin Formulation for Use in Implant not Pumps", Trans Ams Soc Artif Intern Organs, vol. 33, 1987, pp. 316-318.
Washabaugh M.W. et al., "Purfication of Aqueous Ethylene Glycol", Analytical Biochemistry, vol. 134, 1983, pp. 144-152.
Bello J. et al., "Chemical Modification and Cross-Linking of Proteins by Impurities in Glycerol", Archives of Biochemistry and Biophysics, vol. 172, 1976, pp. 608-610.
Robbins D.C. et al., "Antibodies to Covalent Aggregates of Insulin in Blood of Insulin-Using Diabetic Patients", Diabetes, vol. 36, 1987, pp. 838-841.
Robbins D.C. et al., "Free Covalent Aggregates of Therapeutic Insulin in Blood of Insulin-Dependent Diabetics", Diabetes, vol. 36, 1987, pp. 147-151.
Ratner et al., "Persistent Cutaneous Insulin Allergy Resulting From High-Molecular-Weight Insulin Aggregates", Diabetes, vol. 39, 1990, pp. 728-733.

(Continued)

*Primary Examiner*—Christopher R. Tate
*Assistant Examiner*—Marcela M Cordero Garcia
(74) *Attorney, Agent, or Firm*—Thomas E. LaGrandeur; James A. Hoffmann; James J. Kelley

(57) ABSTRACT

The present invention provides means to improve the chemical stability of aqueous, parenteral pharmaceutical compositions comprising a polypeptide and glycerin. Reactive aldehydes are identified in commercial glycerins, and means for reducing such are provided. Convenient means are provided to assay for reactive aldehydes in glycerin, and a strong linear correlation between the level of reactive aldehydes in glycerin and chemical stability of compositions comprising a polypeptide and glycerin is demonstrated. The invention includes aqueous compositions comprising a polypeptide and glycerin having improved chemical stability compared to compositions previously known.

23 Claims, 1 Drawing Sheet

OTHER PUBLICATIONS

Brange J, et al., "Chemical Stability of Insulin. 2 Formation of Higher Molecular Weight Transformation Products During Storage of Pharmaceutical Preparations", Pharmaceutical Research, vol. 9, 1992, pp. 727-734.

Schwendeman S.P. et al., "Stabilization of Tetanus and Diphtheria Toxoids Against Moisture-Induced Aggregation", Proc. Natl. Acad Sci. USA, vol. 92, 1995, pp. 11234-11238.

Fraenkel-Conrat H. et al., "The Reaction of Formaldehyde With Proteins. V. Cross-Linking Between Amino and Guanidyl Groups", JACS, vol. 70, 1948, pp. 2673-2684.

Seetharama Acharya A. et al., "Reaction Of Glycolaldehyde With Proteins: Latent Crosslinking Potential of ∝—Hydroxyaldehydes", Proc. Natl. Acad. Sci. USA, vol. 80, 1983, pp. 3590-3594.

Seetharama Acharya A. et al., "Cross-Linking of Proteins by Aldotriose: Reaction of the Carbonyl Function of the Keto Amines Generated in Situ With Amino Groups", Biochemistry, vol. 27, 1988, pp. 4522-4529.

Brange J., Stability of Insulin, Kluwer Academic Publishers, Boston, 1994, pp. 23-36.

Brange J., et al., "Formulation of Physically Stable Neutral Insulin Solutions for Continuous Infusion by Delivery Systems", Hormone Drugs, Published by the US Pharmacopoeial Convention, Rockville, Maryland, 1982, pp. 96-105.

The European Pharmacopoeia Supplement 2000, Council of Europe, Strasbourg, France, 1999, pp. 747-750.

The British Pharmacopoeia, British Pharmacopoeia Commission, London, 1999, vol. 1, pp. 710-711.

Dickinson R.G. et al., "A New Sensitive and Specific Test for the Detection of Aldehydes: Formation of 6-Mercapto-3Substituted-s-Triazolo(4,3-b)-s Tetrazines", Chemical Communications, 1970, pp. 1719-1720.

Aldrich Technical Information Bulletin No. AL-145, Aldrich Chemical Co,; Hopps, H.B., Aldrichimica Acta 33:28-29, 2000.

Nash, T., "The Colorimetric Estimation of Formaldehyde by Means of the Hantzsch Reaction", Biochem. J., vol. 55, 1953, pp. 416-421.

The International Pharmacipoeia, Third Edition, vol. 4, 1994, pp. 176-181.

Promotional Bulletin Entitled "Discover the Origins of Some of the World's Most Consistently Pure Products; Synthetic Glycerine Products", by Dow Chemical Company—Freeport, TX, USA, pp. 1-32.

Sawicki E., et al., "The 3-Methyl-2-Benzothiazolone Hydrazone Test", Analytical Chemistry, vol. 33, 1961, pp. 93-96.

Paz, M.A., et al., "Determination of Carbonyl Compounds with N-Methyl Benzothiazolone Hydrazone", Archives of Biochemistry and Biophysics, vol. 109, 1965, pp. 548-559.

Eberhardt M.A. et al., "A Colorimetric Procedure for the Determination of Aldehydes in Seawater and in Cultures of Methylotrophic Bacteria", Marine Chemistry, vol. 17, 1985, pp. 199-212.

Glutaraldehyde Test Kit, Model GT-1, Cat. No. 25872-00, by Hach, Loveland, CO, USA.

Bailey B.W. et al., "New Spectrophotometric Method for Determination of Formaldehyde", Analytical Chemistry, vol. 43, 1971, pp. 782-784.

Ziels N.W. et al., "Recovery and Purification of Glycerol", The Journal of the American Oil Chemists Society, vol. 33, 1956, pp. 556-565.

Bello J., "The State of the Tyrosines of Bovine Pancreatic Ribonuclease in Ethylene Glycol and Glycerol", Biochemistry, vol. 8, 1969, pp. 4535-4541.

Riddick J.A. et al., "Organic Solvents", Techniques of Chemistry, vol. 2, Third Edition, pp. 689-691.

Stromquist D.M. et al., "C.P. Glycerol by Ion Exchange", Industrial and Engineering Chemistry, vol. 43, 1951, pp. 1065-1070.

Encyclopedia of Chemical Technology, Fourth Edition, Kirk Othmer, vol. 12, Glycerol, 1994, pp. 681-694.

Remington's Pharmaceutical Sciences, Mack Publishing Company, 18th Edition, 1990, Chapter 66, pp. 1316.

Food Engineering, International Edition, Chilton Company, 1997, p. 14.

Knudsen L.B. et al., "Potent Derivatives of Glucagon-Like Peptide-1 with Pharmacokinetic Properties Suitable for Once Daily Administration", Expedited Articles, Journal of Medical Chemistry, vol. 43, 2000, pp. 1664-1669.

Shome B. et al., "A Reevaluation of the Amino Acid Sewuence of Human Follitropin β-Subunit", Journal of Protein Chemistry, vol. 7, 1988, pp. 325-339.

The United States Pharmacopeia, The National Formulary, United States Pharmacopeial Convention, Inc. 2000, USP 24, NF 19.

Underberg W.J.M. et al., "Separation and Detection Tecniques for Peptides and Proteins in Stability Research and Bioanalysis", Journal of Chromatography B, vol. 742, 2000, pp. 401-409.

Brange J., Galenics of Insulin, Springer-Verlag 1987.

Du Chatinier W.M. et al., "Rapid Stability Indicating UV-Assay of Methenamine Madelate in Tablets Using Solid Phase Extraction", Analytical Letters, vol. 22, 1989, pp. 875-883.

European Pharmacopoeia, Council of Europe, Strasbourg, 1997, pp. 906-907.

Roach P. et al., "Improved Postprandial Glycemic Control During Treatment with Humalog Mix25, A Novel Protamine-Based Insulin Lispro Formulation", Diabetes Care, vol. 22, 1999, pp. 1258-1261.

Peter Schindler, Certificate fom Merck KGaA, Darmstadt, Germany (2001).

Havelund S and Brange J, Abstract, Second Assisi International Symposium, Chemical Stabilization of Insulin-Glycerol Mixtures, Novo Research Institute, Bagsvaerd Denmark (1986).

Ja Rozandeal, Vector Control—Methods for Use by Individuals and Communities, pps 505-513, (1997).

J. Brange,et al., Chemical Stability of Insulin, Acta Pharm., 4(3) 149-155 (1992).

Ullmann's Encyclopeida of Industrial Chemistry, Fifth, Completely Revised Edition, vol. A12.

S. Haveland and J. Brange, Poster Second Assisi International Symposium, Chemical Stabilization of Insulin-Glycerol Mixtures, (1986).

Peter Klusmann, Novo Nordisk, Grounds for Appeal filed with the German Federal Patent Court Against the German Patent Office in Proceedings relating to the German Utility Model that Corresponds to this *U.S. Appl. No. 10/130,836. German Original, English Translation, and Original Cited Supporting Documents.* (Dec. 17, 2004).

* cited by examiner

POLYPEPTIDE COMPOSITIONS WITH IMPROVED STABILITY

This application is a United States national stage application filed under 35 U.S.C. §371 from International Application No. PCT/US00/32421, filed Dec. 5, 2000, which claims benefit of U.S. Provisional Application 60/171,135, filed Dec. 16, 1999, Japanese Patent Application 377208/99, filed Dec. 28, 1999, and U.S. Provisional Application 60/181,030, filed Feb. 8, 2000, each of which application is entirely incorporated herein by reference.

FIELD OF THE INVENTION

This invention is in the field of human medicine. In particular, this invention is in the field of pharmaceutical compositions for treating various diseases, including diabetes and hyperglycemia.

BACKGROUND OF THE INVENTION

Many polypeptide pharmaceutical compositions are utilized for the treatment of diseases in humans and other mammals. Due to their high lability following oral delivery, polypeptide drugs must generally be delivered by parenteral routes. Chief among these routes are subcutaneous, intramuscular and intravenous.

Polypeptide drug products are traditionally supplied to pharmacies, hospitals and patients as solutions, suspensions, or lyophilized products. In liquid form, each polypeptide drug formulation requires a certain minimum level of chemical and physical stability for a defined length of time governed by treatment regimen, patient convenience, patient safety and regulatory guidelines.

To avoid pain or possible tissue damage, liquid polypeptide drug compositions are designed to provide tonicity or osmolarity close to that of the bodily fluids at or surrounding the site of administration. Excipients such as glycerin, dextrose, mannitol, lactose and salts such as sodium chloride are often used for this purpose. Examples of polypeptide drug products employing glycerin as an isotonicity agent include those comprising as active agent human insulin, insulin lispro, insulin aspart and glucagon.

Glycerin has also been used in pharmaceutical compositions as a solubilizer, wetting agent, emulsifier, solvent, bulking substance, antioxidant, chelating agent and preservative [Spiegel, A. J., et al., J. Pharm. Sci. 52:917–927 (1963); Wang, Y-C. J, et al., J. Parenteral Drug Assoc. 34:452–462 (1980); Remington's Pharmaceutical Sciences, Mack Publishing Company 18$^{th}$ Edition, p. 1316 (1990); Li, S., et al., J. Pharm. Sci. 85:868–872 (1996); Sieger, G. M., et al., U.S. Pat. No. 4,016,273, issued 5 Apr. 1977; Heinz, D. N., WIPO publication WO98/29131, 9 Jul. 1998].

For some polypeptide formulations, physical instability precludes the use of salts for isotonicity, a problem often solved by employing glycerin. Glycerin, however, is known to contribute to chemical instability in polypeptide products. In particular, impurities present in glycerin, such as aldehydes, are believed to initiate covalent crosslinking reactions leading to polypeptide dimers and polymers. See, for example, Bello, J., et al. [Arch. Biochem. Biophys. 172: 608–610 (1976)]. For insulin products, such dimers and polymers have been linked to antigenicity and cutaneous allergy as described in Robbins, D. C., et al. [Diabetes 36:838–841 (1987)]; Robbins, D. C., et al. [Diabetes 36:147–151 (1987)]; and Ratner, R. E., et al. [Diabetes 39:728–732 (1990)]. Brange, J., et al. [Pharm. Res. 9:727–734 (1992)] concluded that covalent insulin dimers and polymers should be minimized to avoid these allergic reactions but no methods to achieve this goal were disclosed or suggested.

Three observations may be made about the problem of preparing reliably stable polypeptide compositions containing glycerin for parenteral administration. First, there has been a lack of a simple but accurate assay for determining the level of reactive aldehydes present in glycerin that lead to crosslinked polypeptide impurities. Second, there has been no teaching or suggestion in the prior art that commercial lots of glycerin manufactured from different sources should be evaluated to determine if certain sources are better than others in minimizing the polypeptide crosslinking reactions. Third, there has been no convenient, efficient way of lowering the reactive aldehyde content of glycerin to eliminate or minimize the aldehyde-induced crosslinking reactions in aqueous, pharmaceutical polypeptide compositions. Each of these three observations will now be described in more detail.

Measuring Reactive Aldehydes in Glycerin

The lack of a simple, reliable method of measuring the reactive aldehyde impurities in glycerin that lead to formation of crosslinked polypeptide impurities has hindered solution of the polypeptide crosslinking problem in formulations containing glycerin.

Formaldehyde can initiate crosslinking of polypeptides by a reactive imine link [Schwendeman, S. P., et al., PNAS 92:11234–11238 (1995) and Fraenkel-Conrat, H., et al., JACS 70:2673–2684 (1948)]. Glyceraldehyde and glycolaldehyde react with amino groups in polypeptide solutions, forming crosslinked polypeptides as described in Acharya, A. S., et al. [PNAS 80:3590–3594 (1983)] and Acharya, A. S., et al. [Biochemistry 27:4522–4629 (1988)].

Aldehyde impurities in glycerol were speculated to be involved in formation of high molecular weight polymers in insulin formulations [Brange J., et al., Pharm. Res. 9:727–734 (1992); Brange, J., Stability of Insulin, Kluwer Academic Publishers, Boston, pp. 23–36 (1994); Brange, J., et al., Hormone Drugs, Published by the US Pharmacopoeial Convention, Rockville, Md., pp. 95–105 (1982)] but no methods to quantitate or remove the aldehyde impurities to improve chemical stability of the insulin formulations were disclosed.

There are many assays for aldehydes in the literature, but their applicability to measuring the reactive aldehyde content of glycerin as a predictor of polypeptide crosslinking in pharmaceutical formulations is questionable.

The European Pharmacopoeia Supplement 2000 [Council of Europe, Strasbourg, France, pp. 747–751 (1999)] describes an aldehyde test in its glycerol monograph. This test employs pararosaniline hydrochloride reagent and a 5 ppm formaldehyde standard solution as the comparator.

The British Pharmacopoeia 1999 [British Pharmacopoeia Commission, London, pp. 710–711 (1999)] discloses a test for aldehydes and reducing substances in glycerin using pararosaniline hydrochloride and visual comparison with a standard solution containing 5 ppm of formaldehyde.

The "Purpald" reagent, 4-amino-3-hydrazino-5-mercapto-1,2,4-triazole [Dickinson, R. G., et al., Chem. Commun. p. 1719 (1970)] reacts with aldehydes and has been used for determination of formaldehyde in air, glycols, vaccines, resins and plastic products and detection of acetaldehyde in liver tissue sections and fruit [Aldrich Technical Information Bulletin No. AL-145, Aldrich Chemical Co.; Hopps, H. B., Aldrichimica Acta 33:28–29 (2000)].

The reaction of formaldehyde with acetylacetone to form a colored product was described by Nash, T. [Biochem. J. 55:416–425 (1953)]. This reagent appeared to be fairly specific for formaldehyde, as interference from acetaldehyde was only 1% on a molar basis.

The glycerol monograph of The International Pharmacopoeia [Third Edition, WHO, 4:176–181 (1994)], described a test for aldehydes and reducing substances using fuchsin/sulfurous acid solution. Color intensity was compared to a 0.2 M solution of potassium permanganate.

In a promotional bulletin entitled "Discover the Origins of Some of the World's Most Consistently Pure Products; Synthetic Glycerine Products" by Dow Chemical Company (Freeport, Tex., USA), pp. 10–11, UV spectroscopy is used to compare OPTIM™ Glycerine 99.7% USP with less pure glycerin samples. No quantitative assessment of the level of aldehydes or other organic impurities is provided.

Glyceraldehyde reacts with 3-methyl-2-benzothiazolinone hydrazone hydrochloride (MBTH). In Sawicki, E., et al. [Anal. Chem. 33:93–96 (1961)] this reagent was shown to react with DL-glyceraldehyde, but only measurement of formaldehyde in auto exhaust fumes and polluted air was disclosed. Paz, M. A., et al. [Arch. Biochem. Biophys. 109:548–559 (1965)] showed that L-glyceraldehyde reacted with MBTH and disclosed an assay to detect trace quantities of aldehydes in the presence of ketones, keto acids and various types of pyranose carbohydrates during biochemical reactions. Eberhardt, M. A., et al. [Marine Chemistry 17:199–212 (1985)] disclosed the use of MBTH to measure aldehydes, especially formaldehyde, in seawater and bacterial cultures. MBTH is utilized in a commercial assay using glutaraldehyde, or 1,5-pentanedial [Glutaraldehyde Test Kit Model GT-1, Hach (Loveland, Colo., USA)] as a standard. This test uses a color wheel for measuring glutaraldehyde levels as low as 1 mg/L.

Bailey, B. W., et al. [Anal. Chem. 43:782–784 (1971)] showed the reagent p-phenylenediamine reacted with formaldehyde, acetaldehyde and benzaldehyde but was highly selective for formaldehyde. It was used to measure low concentrations of formaldehyde in air.

We have surprisingly discovered a novel MBTH Test using glyceraldehyde as a standard that can be effectively used to accurately determine the level of reactive aldehydes present in glycerin samples. We have also discovered that the level of crosslinking in polypeptide formulations containing glycerin is strongly correlated in a linear relationship with the level of reactive aldehyde in the glycerin used to prepare the formulations as measured by the aforementioned assay. Thus, our novel MBTH Test may be used to readily predict the relative chemical stability of aqueous, parenteral polypeptide compositions comprising glycerin and may also be employed to select suitable lots of glycerin for use in preparing such compositions.

Glycerin Derived from Various Sources

Another hindrance to solving the polypeptide crosslinking problem in formulations containing glycerin has been the failure to recognize the importance of considering the source from which commercial glycerin is manufactured and the process by which the glycerin is manufactured. In particular, there has been no teaching or suggestion that commercial lots of glycerin manufactured from different sources should be evaluated to determine if certain sources are better than others in minimizing the polypeptide crosslinking reactions.

Aldehydes in glycerin form by autocatalytic or thermal oxidation, as noted in Mohr, J., et al. [Canadian Patent Application 2,242,591, published 13 Jul. 1998]. As reported by Ziels, N. W. [J. Amer. Oil Chemists' Soc. 33:556–565 (1956)], the processes used to commercially manufacture and purify glycerin have a great impact on the final purity of the glycerin, regardless of the starting material. Glycerin has been manufactured from many sources, including animal fat, plants, fermentation, chemical synthesis from smaller organic molecules and from propylene. Methods of manufacturing glycerin from these and other sources are well known to those skilled in the art. However, what influence the source has on the level of reactive aldehydes found in lots of commercially manufactured glycerin and on the ultimate chemical stability of aqueous, parenteral polypeptide compositions comprising glycerin has not been explored or determined.

Rohde, T. D., et al. [Trans. Am. Soc. Artif. Intern. Organs, 33:316–318 (1987)] disclosed a new insulin formulation for use in implantable pumps containing about 80% glycerin in which the animal-rendered glycerin used in previous formulations was replaced with glycerin from an unspecified synthetic source that was further purified by the authors using a mixed bed ion exchange column. The new and previous formulations also differed in pH, a key factor influencing extent of crosslinking reactions in insulin formulations. In treating diabetic patients, a longer flow cycle and lower insulin usage with the new formulation suggested improved stability, which was attributed to the difference in pH and the synthetic glycerin's extra purification.

Using the MBTH Test described herein, we have most surprisingly discovered that commercial glycerin lots manufactured from non-animal sources contain lower levels of reactive aldehydes than animal-derived glycerin. This was demonstrated for glycerin derived from plants and propylene. Glycerin derived from propylene has particularly low levels of reactive aldehydes. We also discovered that commercially manufactured glycerin lots derived from plant and propylene sources have a much lower average reactive aldehyde content per month of age than glycerin lots derived from animal sources, which suggests the level of reactive aldehydes increases faster over time in animal derived glycerin than in plant and propylene derived glycerin.

Furthermore, we discovered that aqueous, parenteral pharmaceutical compositions of polypeptides comprising glycerin derived from propylene have improved chemical stability compared to similar compositions prepared with animal derived glycerin.

Lowering Reactive Aldehyde Levels in Glycerin

Finally, no simple, efficient method for lowering the level of reactive aldehydes in glycerin to improve the chemical stability of pharmaceutical polypeptide compositions comprising glycerin has been disclosed.

Bello, J. [Biochemistry 8:4535–4541 (1969)] and Bello, J., et al. [Arch. Biochem. Biophys. 172:608–610 (1976)] sought to prevent crosslinking in a protein solution containing glycerin by purifying the glycerin. The glycerin was first treated with the reducing agent sodium borohydride. The reduction step was followed by treating the glycerin with MB-3 resin to remove inorganic salts, and finally by distillation in vacuo. There was no indication of the level of reactive aldehydes before or after this treatment. The lowered crosslinking achieved by this glycerin purification was short-lived.

Various glycerin purification techniques were also described in Riddick, J. A., et al. [Techniques of Chemistry II: Organic Solvents, Physical Properties and Methods of Purification, Wiley-Interscience, New York, pp. 689–690 (1970)], Diaz, Z., et al. [U.S. Pat. No. 4,683,347, issued 28 Jul. 1987], Stromquist, D. M., et al. [Ind. Eng. Chem. 43:1065–1070 (1951)] and Ziels, referenced earlier, but none involved lowering the level of reactive aldehydes by contacting the glycerin with a polymeric resin comprising free amino groups.

Washabaugh, M. W., et al. [Anal. Biochem. 134:144–152 (1983)] described a cumbersome procedure for lowering aldehyde levels in ethylene glycol which involved reducing with sodium borohydride, diluting 4-fold with water and passing the aqueous solution though four chromatography columns containing different resins. Aldehydes in the solution were reduced by 86% as quantified using MBTH and a glycolaldehyde standard.

Mohr, J., et al., referenced earlier, described purification of ethylene glycol by contacting the solution with a reducing phosphorous compound. Aldehyde levels, as measured with MBTH, were lowered. Murao, et al. [U.S. Pat. No. 5,969,175, issued 19 Oct. 1999] described a method for purifying a nitrile containing an aldehyde by contacting the nitrile with a cation exchange resin carrying a polyamine. There was no suggestion either of these methods would be useful for lowering the reactive aldehyde content of glycerin to improve the chemical stability of polypeptide compositions comprising glycerin.

We have discovered a simple, efficient method of lowering the level of reactive aldehydes in glycerin samples that provides improved chemical stability to polypeptide compositions comprising glycerin. This method avoids the use of reducing agents, avoids necessarily diluting the glycerin and is compatible with direct use of the purified glycerin in formulations containing polypeptides.

The discoveries described above have been combined to provide novel preparations of polypeptide compositions for parenteral administration comprising glycerin that have improved chemical stability compared to polypeptide compositions previously known. These stabilized polypeptide compositions provide increased safety to patients who use them to treat their disease or condition.

BRIEF SUMMARY OF THE INVENTION

Accordingly, one aspect of the present invention is the use of non-animal derived glycerin as the glycerin component in an aqueous, parenteral pharmaceutical composition comprising a polypeptide and glycerin, to improve the chemical stability of the composition. The improved chemical stability is directed to a reduction in the level of covalently crosslinked polypeptides formed because a lower level of reactive aldehydes is present in the glycerin used in preparation of the composition. More specifically, the present invention provides for the use of glycerin derived from plants or propylene to improve the chemical stability of aqueous, parenteral pharmaceutical compositions comprising a polypeptide and glycerin.

Another aspect of the invention is the use of glycerin that has a reactive aldehyde content of less than 8 ppm as the glycerin component in an aqueous, parenteral pharmaceutical composition comprising a polypeptide and glycerin, to improve the chemical stability of the composition.

Another aspect of the invention is an aqueous, parenteral pharmaceutical composition comprising a polypeptide and glycerin wherein the glycerin is derived from a non-animal source.

Another aspect of the invention is an aqueous, parenteral pharmaceutical composition comprising a polypeptide and glycerin, wherein the glycerin has a reactive aldehyde content of less than 8 ppm.

Another aspect of the invention is a process for preparing an aqueous, parenteral pharmaceutical composition comprising, combining water, a polypeptide and non-animal derived glycerin.

Another aspect of the invention is a process for preparing an aqueous, parenteral pharmaceutical composition comprising, combining water, a polypeptide and glycerin having a reactive aldehyde content of less than 8 ppm.

Another aspect of the invention is a process for lowering the level of reactive aldehydes in glycerin comprising, contacting glycerin with a solid drying agent and a polymeric resin comprising free amino groups.

The compositions of the present invention may be in the form of a solution or in a suspension in which the polypeptide remains partially or completely insoluble in the composition. The compositions may also be formed from two-pack type manufactured products in which a polypeptide in solid form is combined with a separate diluent solution comprising glycerin prior to parenteral administration.

The polypeptide in the pharmaceutical compositions of this invention may be chemically synthesized or produced biosynthetically using recombinant DNA techniques.

The invention includes the use of a composition of the present invention as a medicament or for use in preparing a medicament for the treatment of diseases in mammals.

DETAILED DESCRIPTION OF THE INVENTION

Figure 1:
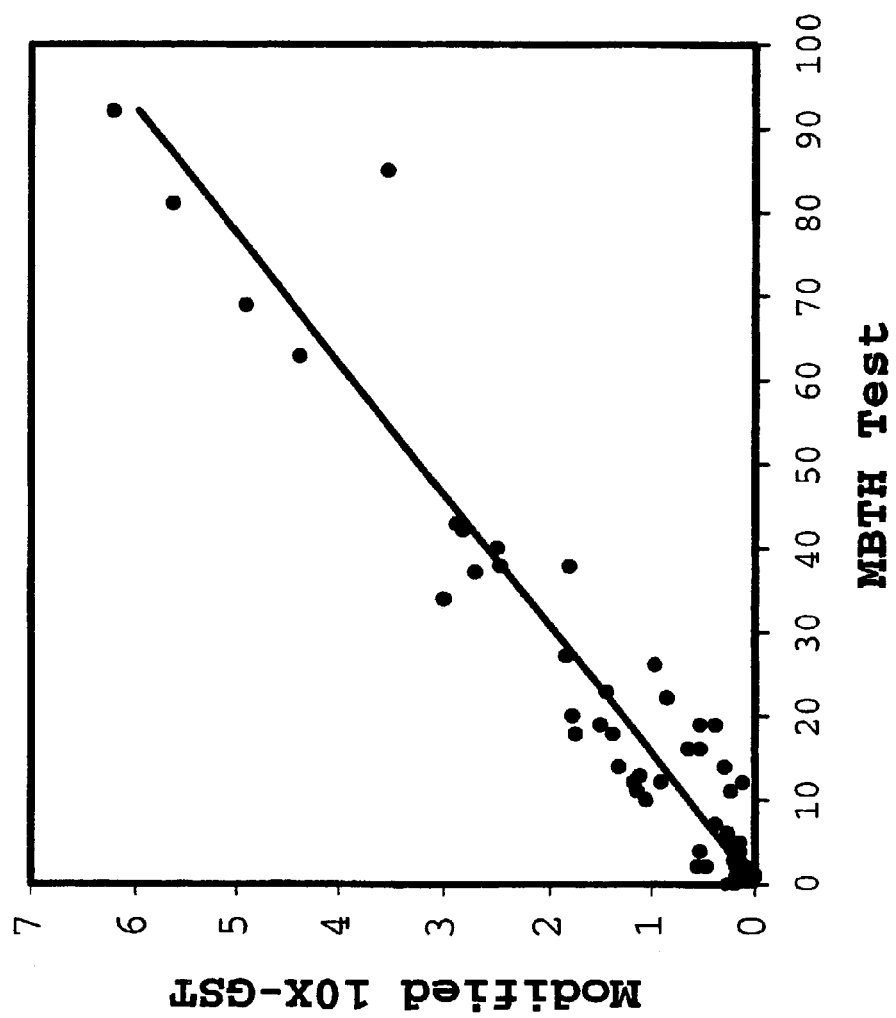
FIG. 1 shows the linear relationship ($R^2=0.90$) between analyses of commercial lots of non-animal derived glycerin determined by the MBTH Test of the present invention and the Modified 10×-GST Test.

The term "glycerin" refers to the chemical propane-1,2,3-triol, CAS Registry Number [56-81-5]. The empirical formula for glycerin is $C(3)H(8)O(3)$, and it has the structure $OH-CH_2-CH(OH)-CH_2-OH$. In some literature reports, the term "glycerol" is used to refer to the chemical compound, "glycerin" refers to purified commercial products containing 95% or more of glycerol, and "glycerine" is used as a commercial name for products whose principal component is glycerol. For the present specification, glycerin, meaning the chemical propane-1,2,3-triol, may be incorporated into the aqueous, parenteral pharmaceutical compositions of the present invention by using any solution comprising the chemical propane-1,2,3-triol. The glycerin concentration in the pharmaceutical polypeptide compositions of the present invention is defined in terms of milligrams of propane-1,2,3-triol per milliliter of the composition and is less than 500 mg/mL.

Glycerin was first discovered in 1779 by Carl W. Scheele, who produced it by heating olive oil with litharge. Since that time, at least five distinct sources of materials have been used to produce glycerin.

One source of glycerin is animals. Tallow or fats from animals such as cattle and sheep are esterified and then saponified in a process that generates glycerin as a by-product of soap manufacturing. Animal fats are also hydrolyzed or saponified directly to generate glycerin.

A second commercial source of glycerin is plants. Generally, oils derived from coconut, palm, canola, soy or other plants are used to generate glycerin by methods comparable to those used with animal fats.

A third source of glycerin is fermentation. Glycerin is fermented from natural sources such as beet molasses or using microorganisms modified with recombinant DNA technology such as those described by Bulthuis, B. A., et al. [WIPO publication WO98/21340, 22 May 1998] and by Nair, R. V., et al. [WIPO publication WO98/28480, 10 Jun. 1999].

A fourth source of glycerin is chemical synthesis starting with organic molecules containing fewer than three carbon atoms. One such procedure, using methanol, is described in Owsley, D. C., et al. [U.S. Pat. No. 4,076,758, issued 28 Feb. 1978].

A fifth source of glycerin is propylene, which itself is obtained from petroleum products. Glycerin produced from propylene became available beginning about 1948. Many synthetic routes converting propylene to glycerin are available, including those described in Owsley, D. C., et al. referenced earlier, in Kirk-Othmer [Encyclopedia of Chemical Technology 12:681–694 (1994)] and in Remington's Pharmaceutical Sciences [Mack Publishing Company, 18$^{th}$ Edition, p. 1316 (1990)]. In one synthetic route, for example, propylene is chlorinated to allyl chloride, followed by conversion with hypochlorous acid to form dichlorohydrin, reaction with calcium hydroxide to generate epichlorohydrin, and finally hydrolysis to glycerin.

Glycerin is available commercially from a variety of sources, suppliers and distributors [see Chemical Week, Special Issue Buyer's Guide, 159:321–322 (1997), and Chemical Industry Europe 93; The Leading Guide for Today's European Chemical Industry (1993)].

Glycerin products derived from plants include Pricerine 9091 [Unichema North America, Chicago, Ill., USA], Kosher Superol Glycerine [Proctor and Gamble Chemicals, Cincinnati, Ohio, USA], Glycerine-99.7% [Chemical Associates of Illinois, Inc., Copley, Ohio, USA], Emery® Glycerine-99.7% Kosher [Henkel Corporation, Cincinnati, Ohio, USA] and Glycerol anhydrous extra pure [EM Industries, Hawthorne, N.Y., USA].

Glycerine products derived from propylene include Optim™ Glycerine 99.7% USP [Dow Chemical Company, Freeport Tex., USA], Glycerin, synthetic [Solvay Fluorides, Inc, Greenwich, Conn., USA] and Optim™ Glycerine 99.7%, [Dow Chemical Company, Stade, Germany]. Glycerin derived from propylene has been used as a flavor facilitator for coating popcorn kernels [Schellhaass, S. R., U.S. Pat. No. 5,750,166, issued 12 May 1998] and used at a low concentration in a surgical lotion [Scholz, M. T., et al., U.S. Pat. No. 5,951,993, issued 14 Sept. 1999]. Glycerin derived from propylene has also been used in food and pharmaceutical preparations [Food Engineering, International Edition (Chilton Company), p. 14 (1997)].

The term "non-animal derived glycerin" refers to glycerin not derived from the fat or any other bulk component of an animal. Sources of manufacture of non-animal derived glycerin include plants, propylene, fermentation and chemical synthesis from smaller organic molecules.

The present invention provides for aqueous, parenteral pharmaceutical compositions comprising a polypeptide and glycerin wherein the glycerin concentration of the composition is less than 500 mg/mL. The glycerin concentration refers to the concentration of the chemical propane-1,2,3-triol. Preferably, the glycerin concentration in the pharmaceutical composition is about 1 mg/mL to about 300 mg/mL. More preferably, the glycerin concentration in the composition is about 3 mg/mL to about 100 mg/mL. More preferably, the glycerin concentration in the aqueous, pharmaceutical, polypeptide composition is about 10 mg/mL to about 30 mg/mL. More preferably, the glycerin concentration in the composition is about 20 mg/mL to about 25 mg/mL. More preferably, the glycerin concentration in the composition is about 22 mg/mL. Another preferred range of glycerin concentration in the composition is about 15 mg/mL to about 18 mg/mL. More preferably, the glycerin concentration in the composition is about 16 mg/mL.

The term "aldehyde" refers to the class of organic compounds containing the CHO radical or functional group.

The term "reactive aldehyde" refers to those aldehydes which are a) present as an impurity in commercial lots of glycerin and, b) reactive with amino groups present in polypeptides in aqueous, pharmaceutical compositions leading to formation of covalent polypeptide dimers and/or polymers. An example of a reactive aldehyde is glyceraldehyde.

The term "MBTH" refers to the chemical 3-methyl-2-benzothiazolinone hydrazone hydrochloride, CAS Registry Number [14448-67-0].

The term "MBTH Test" refers to a method of measuring the reactive aldehyde content in glycerin samples using glyceraldehyde as a standard and is described in detail as Method 1.

The abbreviation "ppm" refers to parts per million on a mass basis. For purposes of the present invention, ppm refers to parts per million of reactive aldehyde present in a sample of glycerin. More particularly, ppm refers to the mass of reactive aldehyde relative to the mass of the glycerin. For example, a MBTH Test value of 2 ppm for a particular lot of glycerin means it contains 2 parts mass of reactive aldehyde per million parts mass of glycerin. This is equivalent to a concentration in the glycerin of 2 ug/gm or 2 mg/kg. If a glycerin sample is diluted with another solvent prior to its analysis, then the ppm results of the test must be multiplied by the dilution to reflect the parts of reactive aldehyde per million parts of the original, undiluted glycerin.

One embodiment of the present invention provides for aqueous, pharmaceutical polypeptide compositions which comprise non-animal derived glycerin. One may prepare pharmaceutical compositions within this embodiment of the invention without measuring the aldehyde content of the glycerin prior to its use. However, the glycerin used in preparing a polypeptide composition is preferably assayed prior to its use and has a reactive aldehyde content of less than 33 ppm. More preferably, the glycerin has a reactive aldehyde content of less than 24 ppm. More preferably, the glycerin has a reactive aldehyde content of 15 ppm or lower. More preferably, the glycerin has a reactive aldehyde content of less than 8 ppm. Most preferably, the glycerin used in the polypeptide compositions of the present invention has a reactive aldehyde content of 3 ppm or lower.

If one chooses to measure the reactive aldehyde content of the glycerin used in preparing a polypeptide composition of the present invention, a variety of assays may be employed. One such assay is the novel HPLC procedure described herein as Method 4. Alternatively, an aldehyde assay known to those skilled in the art may be used. Preferably, the reactive aldehyde content of the glycerin used in the polypeptide compositions of the present invention is measured by an assay wherein glyceraldehyde is used as a standard. More preferably, the reactive aldehyde content of the glycerin is measured by the MBTH Test described herein.

The term "10×-GST" refers to a glycerin stress test incorporating about 10 times more glycerin than normal in a soluble insulin preparation that is designed to accelerate formation of covalent dimers and polymers of the insulin. This test is described in detail below as Method 2.

The term "Mod.10×-GST" refers to a glycerin stress test incorporating about 10 times more glycerin than normal in an insulin suspension composition designed to accelerate formation of covalent dimers and polymers of the insulin. This test is described in detail below as Method 3.

The term "polypeptide" refers to a compound comprising three or more amino acids and at least one free amino group, and includes analogs and derivatives thereof. Polypeptides may be produced by chemical synthesis and/or by biosynthesis using recombinant DNA technology. Polypeptides may contain one or more strands of amino acids connected together by covalent bonds, such as disulfide bonds, or by non-covalent interactions. Small polypeptides may also be referred to herein as "peptides". Large polypeptides may also be referred to herein as "proteins".

Polypeptides incorporated into the compositions of the present invention may contain naturally occurring L-amino acids or unnatural amino acids, such as D-amino acids. The amino acid sequence of the polypeptides may be identical to those occurring naturally in animals or other organisms or may be analogs in which the sequence is altered in various ways. In analogs of polypeptides, one or more amino acids may be added, deleted or replaced by other amino acids at the N-terminal, C-terminal or internal portions of the polypeptide. Analogs of polypeptides are well known in the art.

Polypeptides to be incorporated into the compositions of the present invention may also have an attachment of organic chemical groups on the amino acid side chains, on the N-terminal amino group or on the C-terminal carboxyl group of the polypeptide. Such compounds are examples of polypeptide "derivatives". Other examples of polypeptide derivatives include glycopeptides in which naturally occurring polysaccharides are attached to the side chains of the amino acids asparagine or threonine. Other derivatizing groups that may be attached to polypeptides include acyl groups and polyethylene glycol. Derivatives of polypeptides are well known in the art.

A polypeptide incorporated into the compositions of the present invention may be present in a variety of forms, including a pharmaceutically acceptable salt form. A pharmaceutically acceptable salt of a polypeptide means a salt formed between any one or more of the charged groups in the polypeptide and any one or more pharmaceutically acceptable, non-toxic cations or anions. Organic and inorganic salts include, for example, ammonium, sodium, potassium, Tris, calcium, zinc or magnesium and those prepared from acids such as hydrochloric, sulfuric, sulfonic, tartaric, fumaric, glycolic, citric, maleic, phosphoric, succinic, acetic, nitric, benzoic, ascorbic, p-toluenesulfonic, benzenesulfonic, naphthalenesulfonic, propionic, carbonic, and the like.

The polypeptides incorporated into the compositions of the present invention may be isolated from sources such as transgenic plants or transgenic animals or may be prepared by chemical synthesis techniques including classical (solution-phase) methods, solid phase methods, semi-synthetic methods or other methods well known to those skilled in the art.

The polypeptides incorporated into the compositions of the present invention may also be produced biosynthetically using recombinant DNA technology. For example, see Chance, R. E., et al., U.S. Pat. No. 5,514,646, issued 7 May 1996; Chance, R. E., et al., EPO publication number 383,472, 7 Feb. 1996; Brange, J., et al., EPO publication number 214,826, 18 Mar. 1987; and Belagaje, R. M., et al., U.S. Pat. No. 5,304,473, issued 19 Apr. 1994. Using rDNA technology, polypeptides or precursors thereof may be biosynthesized in any number of host cells including bacteria, mammalian cells, insect cells, yeast or fungi. More preferred is biosynthesis in bacteria, yeast or mammalian cells. Most preferred is biosynthesis in *E. coli* or a yeast. Examples of biosynthesis in mammalian cells and transgenic animals are described in Hakola, K. [Molecular and Cellular Endocrinology, 127:59–69, (1997)].

Specifically excluded polypeptides for incorporation into the compositions of the present invention are naturally occurring polypeptides isolated from tissues, glands, organs, blood, urine or any other bulk component of non-transgenic animals. An example of an excluded polypeptide is pork insulin that is produced from the pancreas of pigs.

The present invention is believed to apply to any polypeptide and includes, inter alia, antibodies, cytokines, receptors, polypeptide hormones, and fragments thereof. The compositions of the present invention may also comprise more than one polypeptide. Without limiting the generality of the scope of the present invention, several specific polypeptides and groups of polypeptides will be named to better instruct the reader.

A preferred group of polypeptides for inclusion in the compositions of the present invention consists of recombinant human insulin, recombinant pork insulin and recombinant beef insulin.

Another preferred group of polypeptides for inclusion in the compositions of the present invention consists of monomeric insulin analogs. For example, see Balschmidt, P., et al., U.S. Pat. No. 5,164,366, issued 17 Nov. 1992; Brange, J., et al., U.S. Pat. No. 5,618,913, issued 8 Apr. 1997; Chance, R. E., et al., U.S. Pat. No. 5,514,646, issued 7 May 1996; and Ertl, J., et al., EPO publication number 885,961, 23 Dec. 1998. Particularly preferred are those monomeric insulin analogs wherein the amino acid residue at position B28 is Asp, Lys, Ile, Leu, Val or Ala and the amino acid residue at position B29 is Lys or Pro. The most preferred monomeric insulin analogs are Lys(B28)Pro(B29)-human insulin, Asp(B28)-human insulin and Lys(B3)Ile(B28)-human insulin.

Another preferred group of polypeptides for inclusion in the compositions of the present invention consists of insulin analogs wherein the isoelectric point of the insulin analog is between about 7.0 and about 8.0. These analogs are referred to as pI-shifted insulin analogs. A most preferred group of pI-shifted analogs consists of Arg(B31)Arg(B32)-human insulin and Gly(A21)Arg(B31)Arg(B32)-human insulin.

Another preferred group of polypeptides for inclusion in the compositions of the present invention consists of derivatives of insulin and derivatives of insulin analogs. A more preferred group of polypeptides for inclusion in the compositions of the present invention consists of acylated derivatives of insulin and acylated derivatives of insulin analogs. A more preferred group of polypeptides consists of acylated derivatives of insulin and acylated derivatives of insulin analogs wherein the acyl group consists of straight-chain, saturated fatty acids. Examples of straight-chain, saturated fatty acids include carbon lengths C4, C6, C8, C10, C12, C14, C16 and C18. The most preferred group of polypeptides for inclusion in the compositions of the present invention consists of palmitoyl-ε-Lys (B29)-human insulin and myristoyl-ε-Lys (B29)-des (B30)-human insulin, wherein the palmitoyl (C16) and myristoyl (C14) straight chain fatty acids are attached to the epsilon (ε) amino group of the Lys (B29) residue.

Another preferred group of polypeptides for incorporation into the compositions of the present invention consists of glucagon-like peptide-1 (GLP-1), GLP-1 analogs, derivatives of GLP-1 and derivatives of GLP-1 analogs. By custom in the art, the amino-terminus of GLP-1(7-37)OH has been assigned number 7 and the carboxyl-terminus has been assigned number 37. A more detailed description of GLP-1 analogs and derivatives is found in Hoffmann, J. A. [WO99/29336, published 17 Jun. 1999] and in Knudsen, L. B., et al. [J. Med. Chem. 43:1664–1669 (2000)]. An example of a derivative of a GLP-1 analog is Arg(34), N-ε-(γ-Glu(N-α-hexadecanoyl))-Lys(26)-GLP-1 (7-37)OH, described by Nielson, J., et al. [WO00/07617, published 17 Feb. 2000]. A more preferred group of polypeptides for incorporation into the compositions of the present invention consists of native GLP-1(7-36)NH2, native GLP-1(7-37)OH, Val(8)-GLP-1 (7-37)OH, Gly(8)-GLP-1(7-37)OH and Arg(34), N-ε-(γ-Glu (N-α-hexadecanoyl))-Lys(26)-GLP-1(7-37)OH.

Another preferred group of polypeptides for inclusion in the compositions of the present invention consists of exendin, exendin analogs, derivatives of exendin and derivatives of exendin analogs. Exendin polypeptides and analogs include exendin-3 and exendin-4, described by Young, A., et al. [WIPO publication WO00/41546, 20 Jul. 2000]. Examples of derivatives of exendin and derivatives of exendin analogs are those described by Knudsen, et al. [WIPO publication WO99/43708, 2 Sep. 1999]. A more preferred polypeptide for use in the compositions of the present invention is exendin-4.

Another preferred group of polypeptides for incorporation into the compositions of the present invention consists of granulocyte colony-stimulating factor (G-CSF), described by Goldenberg, M. S., et al. [WIPO publication WO00/38652, 6 Jul. 2000], G-CSF analogs, G-CSF derivatives and derivatives of G-SCF analogs. G-CSF compositions of the present invention may be in solution or suspension form. A suspension composition of G-CSF is preferred.

Another preferred group of polypeptides for incorporation into the compositions of the present invention consists of leptin, leptin analogs, derivatives of leptin and derivatives of leptin analogs. A more preferred group of polypeptides consists of glycosylated leptin analogs. A more detailed description of the sequence of native leptin and examples of leptin analogs is found in Beals, J. M., et al. [EPO publication number 849,276, 24 Jun. 1998].

Another preferred group of polypeptides for incorporation into the compositions of the present invention consists of the full length human parathyroid hormone PTH(1–84), fragments such as PTH(1–38) and PTH(1–34), and analogs and derivatives thereof [see Chang, C-M., et al., WIPO publication WO99/29337, 17 Jun. 1999]. A more preferred group of polypeptides consists of human PTH(1–34) and human PTH(1–84).

Another preferred group of polypeptides for incorporation into the compositions of the present invention consists of recombinant follicle stimulating hormone (FSH) and recombinant analogs and derivatives thereof. FSH is a heterodimeric glycoprotein in which the alpha and beta subunits bind non-covalently, as described in Shome, et al. [J. Prot. Chem., 7:325–339, (1988)]. A more preferred group of polypeptides consists of recombinant human FSH and recombinant analogs of FSH in which one, two, three or more C-terminal amino acid residues of the naturally encoded beta subunit are deleted, and glycosylation derivatives thereof.

Another preferred group of polypeptides for incorporation into the compositions of the present invention consists of recombinant human growth hormone (HGH), recombinant bovine growth hormone (BGH) and analogs and derivatives thereof. A more preferred group of polypeptides consists of recombinant HGH and recombinant BGH.

A preferred polypeptide that may be incorporated into the aqueous, parenteral pharmaceutical compositions of the present invention is FSH or an analog or derivative thereof, PTH or a fragment, analog or derivative thereof, HGH or an analog thereof, human leptin or an analog or derivative thereof, GLP-1 or an analog or derivative thereof, human insulin or an analog or derivative thereof, or a derivative of a human insulin analog.

More than one polypeptide may be incorporated into the aqueous, parenteral pharmaceutical compositions of the present invention. Examples of such combinations include, inter alia, mixtures of amylin or an amylin agonist peptide and an insulin as described by Cooper, G. J. S. [U.S. Pat. No. 5,124,314, issued 23 Jun. 1992] and L'Italien, J., et al. [U.S. Pat. No. 6,136,784, issued 24 Oct. 2000].

The polypeptides in the pharmaceutical compositions of the present invention are biologically active. This activity may be demonstrated in vitro or in vivo and results from interaction of the polypeptide with receptors and/or other intracellular or extracellular sites leading to a biological effect.

The term "aqueous" describes a liquid solvent that contains water. Aqueous solvent systems may be comprised solely of water, or may be comprised of water plus one or more miscible solvents, and may contain dissolved solutes such as sugars or other excipients.

The term "aqueous, parenteral pharmaceutical composition" used in the present invention means a pharmaceutical composition for parenteral administration wherein the water content is 500 mg/mL or greater.

The term "pharmaceutical" means containing a medicinal substance or preparation used in treating disease. The pharmaceutical compositions of the present invention contain polypeptides with biological activity. The compositions are prepared in a manner suitable for and consistent with their pharmaceutical use.

The term "parenteral" means delivery or administration of a drug to a patient in need thereof other than through the intestine. Preferred routes of parenteral administration of the polypeptide compositions of the present invention are subcutaneous, intramuscular, intravenous, buccal, nasal, pulmonary, intraocular and transdermal.

The term "chemical stability" refers to the relative rate of formation of covalently bonded polypeptide dimers and polymers initiated by reactive aldehydes in a polypeptide composition. A "stable" formulation is one wherein the rate of formation of covalent polypeptide dimers and polymers is acceptably controlled and does not increase unacceptably with time. The term "improved" in reference to the chemical stability of a specified composition means its level of increased high molecular weight polypeptide dimers and polymers after a period of time is lower than the level in a comparably prepared and treated composition. Chemical stability may be assessed by methods well known in the art.

Examples of measuring chemical stability by size exclusion HPLC are included in the 10×-GST and Modified-10×-GST methods described herein.

Early in the development of a polypeptide formulation for pharmaceutical use, experiments are conducted to determine which excipients should be included in the formulation. Formulations are usually designed to comprise the fewest number and quantities of excipients necessary to provide an efficacious product that meets the safety and stability needs of the patient and regulatory agencies. Stability requirements include physical stability and chemical stability.

In formulations employing glycerin, the reactive aldehyde-initiated covalent crosslinking of polypeptides must be minimized during the normal storage of the manufactured product. As an example, for insulin solutions, the level of high molecular weight protein must remain below 1.5% throughout the refrigerated shelf-life of the product [USP 2000, United States Pharmacopeial Convention, Inc., Rockville, Md., USA (1999)]. Manufacturers strive to consistently meet this type of shelf-life specification to guarantee the safety of the product to the patient.

For glycerin-containing polypeptide compositions, the reactive aldehyde-initiated covalent polymerization reaction is an area of concern. It would not be prudent to incorporate just any lot of commercial glycerin into polypeptide formulations for human use without proper reactivity testing. In fact, every batch of glycerin obtained from a commercial source could be evaluated in some manner to ensure that polypeptide products formulated with it will meet stability specifications.

One way of testing the suitability of glycerin is to prepare small batches of the actual pharmaceutical product and then evaluating polymer formation, generally by HPLC, throughout the normal shelf-life period and under normal storage conditions. A variety of separation and detection techniques for analyzing polypeptides in stability studies is described by Underberg, W. J. M., et al. [J. Chromatography B 742:401–409 (2000)]. This testing approach, however, is impractical since it takes too long and requires excessive analytical resources.

A better way to assess the suitability of commercial glycerin lots is to accelerate the rate of covalent polypeptide polymer formation. These reactions may be accelerated by increasing the storage temperature [Brange, J., Galenics of Insulin, Springer-Verlag (1987)], by increasing the level of glycerin above the normal level, or both. Two examples of accelerated "stress" tests are the 10×-GST Test and Modified 10×-GST Test described as Methods 2 and 3 below.

In typical U100 insulin products, insulin is present at a concentration of 3.5 mg/mL, or about 600 nmoles/mL. The glycerin level found in normal insulin formulations is 16 mg/mL, or about 174,000 nmoles/mL. If the level of reactive aldehyde in a lot of glycerin is, for example, 10 ppm, then the concentration of reactive aldehyde in normal insulin formulations would only be about 1.74 nmoles/mL, or 345-fold less than the insulin. Increasing this glycerin level 10-fold provides a composition in which the reactive aldehydes are still 34-fold lower than insulin on a molar basis, but will increase the rate of reaction between the reactive aldehydes and the insulin molecules. For the accelerated tests described in Method 2 and Method 3, both elevated temperature (30° C.) and elevated glycerin levels (10-fold) are employed.

Under properly controlled conditions, accelerated stability tests reliably predict the relative stability of manufactured polypeptide formulations. This is because all of the ingredients used in the final formulation are contained in the test solutions.

From the results of the accelerated stability tests, the relative rates of covalent polymer formation are correlated with rates of formation under normal storage conditions. This correlation is based on analytical considerations, e.g. by using the Arrhenius equation for a range of temperatures, by using quantitative calculations based on the proposed mechanism of reaction of each molecule of reactive aldehyde with up to two molecules of the polypeptide, and/or by comparing the relative polymer formation rates in the formulations. Methods to establish a specification limit for stability of polypeptide compositions are well known to those skilled in the art. From these considerations, a maximum level of polymer formation in an accelerated test, for example 1% per week at 30° C., may be established as a specification limit which must be met to provide a high degree of assurance that satisfactory stability under normal shelf-life conditions will be achieved.

Despite the reliable results obtained, there are many disadvantages to the accelerated methods of formulation lot evaluation. First, the preparation of multiple samples of the pharmaceutical compositions takes a great deal of time, especially if they must be prepared in a manner identical to the method used to prepare manufactured compositions. Since the reaction rates of the reactive aldehydes with each polypeptide in each different formulation are unpredictable, each polypeptide formulation must be tested independently. Second, the preparation of multiple samples of polypeptide compositions wastes precious material and is especially wasteful of the therapeutic polypeptide itself. Third, although the crosslinking reactions can be accelerated, the time needed to generate enough crosslinked impurity to permit reliable quantitation may take a week or longer. Fourth, the assay procedures for determining the level of crosslinked products in the polypeptide compositions are complex, time consuming and costly. The assay methods typically involve analysis by HPLC, which requires specialized columns, specialized training for the operators and a considerable length of time to run the assays, collect the data and interpret the results.

Direct analysis of each batch of glycerin circumvents the disadvantages of the accelerated stability tests.

One aspect of the present invention is a method of determining the identity and level of reactive aldehydes in glycerin. In particular, a novel HPLC procedure (Method 4) was developed to determine which aldehydes are present in commercial lots of glycerin and their relative concentrations. The results showed that, for all sources of glycerin tested, glyceraldehyde was the major aldehyde impurity, with much lower levels of formaldehyde and even lower levels of glycolaldehyde present. Formaldehyde levels were somewhat higher in plant-derived glycerin than in animal and propylene-derived glycerin.

As a screening test for glycerin lots, though, this method has the disadvantages associated with HPLC analysis described above.

Another aspect of the present invention is providing a novel colorimetric assay, using glyceraldehyde as a standard, that simply and reliably quantifies the reactive aldehyde content of commercial lots of glycerin. This assay is the MBTH Test described in detail as Method 1 below. As shown in Example 1, this assay provides a very high molar absorptivity upon reaction with glyceraldehyde, which the HPLC assay (Method 4) identified as the predominant aldehyde in commercial lots of glycerin.

Most usefully, the MBTH Test shows an excellent linear correlation between the reactive aldehyde content of the glycerin and the increased level of covalent dimers and polymers measured in an accelerated stability test, namely, the Modified 10×-GST Test (see Example 2 and FIG. 1). Good correlation factors were obtained with the glycerin lots derived from animals, plants and propylene. A simple, direct analysis of glycerin lots using the MBTH Test has been invented to replace the inefficient accelerated tests employing polypeptide formulations, extensive incubation times and complex HPLC systems.

To obtain a specification limit for the reactive aldehyde level determined by the MBTH Test, one may simply use the correlation line, e.g. as shown in FIG. 1, to find the MBTH reactive aldehyde level that intersects at the line with the specification limit determined by the accelerated stability test. For example, from FIG. 1, a specification limit of 1% polymer growth determined by the Modified 10×-GST Test results in a specification limit of 14 ppm for the MBTH Test. The specification limit is the highest level of reactive aldehyde (e.g. as measured by the MBTH Test) allowed in glycerin lots to be used in preparing the manufactured polypeptide compositions. If lower levels of crosslinked polypeptides or a greater assurance that the compositions will pass the requisite shelf-life stability are desired, then lower specification limits may be established.

Based on these considerations, the maximum general specification limit for reactive aldehyde content in non-animal derived glycerin for use in preparing aqueous, parenteral pharmaceutical polypeptide compositions of the present invention, if assayed, is 33 ppm. A more preferred specification limit for non-animal derived glycerin is 24 ppm. A more preferred specification limit is 15 ppm. A more preferred specification limit is 8 ppm. The most preferred specification limit is 3 ppm. Preferably, if the reactive aldehyde content of the glycerin is measured prior to its use in preparing a composition, the assay uses glyceraldehyde as a standard. More preferably, if the reactive aldehyde content of the glycerin is measured prior to its use in preparing a composition, the assay used is the MBTH Test described herein.

We have used the MBTH Test to evaluate fresh and aged commercial glycerin lots obtained from several manufacturers. Most surprisingly, we found that animal derived glycerin had a higher range of reactive aldehyde content (10–1069 ppm, n=19) than glycerin derived from plants (4–153 ppm, n=29) or glycerin derived from propylene (0–169 ppm, n=41). The average reactive aldehyde level of glycerin lots derived from animals was also higher than glycerin lots derived from non-animal sources.

The MBTH Test described herein was also used to evaluate commercial glycerin lots whose date of manufacture, ranging from 1–48 months prior to assay, were known. These tests, described in Example 3, clearly showed that, at comparable ages, glycerin lots derived from plants or propylene averaged much lower levels of reactive aldehydes than glycerin lots manufactured from animals. Due to the inherent uncertainties in the manufacturing processes and storage time and storage conditions used by glycerin manufacturers, suppliers and shippers, these data show a clear advantage for selecting non-animal derived sources of glycerin for preparation of polypeptide compositions for parenteral use. Since reactive aldehyde levels increase with age even for non-animal derived glycerins (see Table 2), it is also advantageous to select the freshest available commercial lots of glycerin for use in preparing polypeptide compositions.

In considering various commercial sources of glycerin for use in preparing polypeptide compositions, non-animal derived glycerin is clearly preferable. More preferred are commercial lots of glycerin derived from propylene or plants. Using non-animal derived glycerin rather than animal derived glycerin in aqueous, parenteral pharmaceutical polypeptide compositions will generally result in improved chemical stability due to a lower reactive aldehyde content in the glycerin. The correlation of improved chemical stability with lower reactive aldehyde content in the glycerin is illustrated for compositions of a leptin analog, human insulin and insulin analogs in Examples 4–8 described herein.

A preferred embodiment of the present invention is the use of non-animal derived glycerin as the glycerin component in an aqueous, parenteral pharmaceutical composition comprising a polypeptide and glycerin, to improve the chemical stability of the composition. A more preferred embodiment is the use of glycerin derived from a propylene or plant source as the glycerin component in an aqueous, parenteral pharmaceutical composition comprising a polypeptide and glycerin, to improve the chemical stability of the composition. A most preferred embodiment is the use of glycerin derived from propylene as the glycerin component in an aqueous, parenteral pharmaceutical composition comprising a polypeptide and glycerin, to improve the chemical stability of the composition. Examples 9–26 and 28–34 describe the preparation of polypeptide compositions incorporating glycerin derived from non-animal sources.

The improved chemical stability of a polypeptide composition of the present invention means its level of increased high molecular weight polypeptide dimers and polymers after a period of time is lower than the level in a similarly treated comparative composition. The formation of covalent dimers and polymers may be quantified in tests conducted under a variety of conditions, times and temperatures. Examples 4 to 8 of the present specification provide results of tests in which lower levels of increased high molecular weight dimers and polymers are evident in polypeptide compositions of the present invention after specified periods of time and temperature. Preferably, the improved chemical stability of polypeptide compositions of the present invention results in a level of increased high molecular weight dimers and polymers that is at least 3% lower than the level in comparable compositions previously known. More preferably, the level of increased dimer and polymer formation is at least 10% lower. More preferably, the level of increased dimer and polymer formation is at least 30% lower. Most preferably, the level of increased high molecular weight dimers and polymers in compositions of the present invention is at least 60% lower than the level in previously known compositions.

Another preferred embodiment of the present invention is an aqueous, parenteral composition comprising a polypeptide and glycerin wherein the glycerin is derived from a non-animal source. A more preferred embodiment is a polypeptide composition comprising glycerin wherein the glycerin is derived from plants or propylene. The most preferred embodiment is a polypeptide composition comprising glycerin wherein the glycerin is derived from propylene.

As can be seen from the data in Table 2, selecting a commercial glycerin lot derived from non-animal sources does not guarantee that an extremely low reactive aldehyde level, e.g. 3 ppm or less, will be obtained. For any pharmaceutical polypeptide composition being prepared, purchased lots of commercial glycerin from either animal or non-animal derived sources may not have a reactive aldehyde level low enough to meet the specification limit that is desired.

Thus, another aspect of the present invention is a process for lowering the reactive aldehyde content of glycerin. In particular, as described in Example 8, the method comprises contacting glycerin with a solid drying agent and a polymeric resin comprising free amino groups.

The type of amine-containing resin, the nature of the drying agent and the physical configuration of the contact between the glycerin, polymer and drying agent are not thought to be critical to the removal of the reactive aldehydes.

Amine-containing polymeric resins that may be utilized in this aspect of the invention include polystyrene-based resins such as Tris (2-aminoethyl) amine polystyrene resin, TantaGel® S NH2 resin and aminomethyl polystyrene resin. A preferred resin is aminomethyl polystyrene resin.

A wide range of quantities of the amine-containing polymeric resin may be employed in this aldehyde-lowering process. It is preferred that a large molar excess of the amine-containing polymeric resin, compared to aldehyde in the glycerin, be employed to accelerate the process and to maximize the reactive aldehyde-lowering effect.

Contact between the glycerin, polymeric resin and drying agent may be effected by passing the glycerin through an immobilized solid aggregate that comprises the solid drying agent and the resin. The immobilized solid aggregate itself may be housed in a cylindrical column. This type of physical configuration may facilitate passage of the glycerin through the immobilized solid aggregate such that large volumes of glycerin with lower reactive aldehyde levels may be quickly and efficiently obtained.

Alternatively, contact may be effected in a batch process in which the solid drying agent and the polymeric resin are added to the glycerin to form a suspension. In the batch process, preferred subsequent steps include heating the suspension to between about 40° C. and about 100° C., stirring the heated suspension for about 1 minute to about 100 hours, passing the suspension through a filter that retains the solid drying agent and the polymeric resin and then collecting the glycerin passing through the filter. Glycerin treated by the batch process will have its reactive aldehyde content lowered. This batch process may also be utilized to lower very quickly and efficiently the reactive aldehyde level of very large volumes of glycerin.

Many techniques for separating the polymer and drying agent from the purified glycerin are also operable. Phase separation techniques that may be utilized for this aspect of the invention include centrifugation and filtration. Filtration is a preferred method. A variety of filtration equipment and procedures is suitable for phase separation, including filters comprised of cellulose or fiberglass. A fiberglass filter is preferred. A more preferred filter is a Corning 5 micron fiberglass membrane, Part #25981-PF (Corning Inc., Corning, N.Y., USA).

In the batch process, it is not essential, but preferred, that a non-oxidizing environment be maintained around the glycerin being purified as much as possible, especially during the heating and stirring steps. This non-oxidizing environment may be obtained by providing an inert atmosphere above the glycerin, for example, by using a glovebag or purging the glycerin with argon or nitrogen, or by providing a reduced atmosphere or partial vacuum.

Providing a nitrogen atmosphere during the glycerin heating and stirring steps is more preferred.

Although the nature of the drying agent is not believed to be critical for the success of the aldehyde-lowering process, preferred drying agents for use in this aspect of the invention include magnesium sulfate ($MgSO_4$) and calcium chloride ($CaCl_2$). A more preferred drying agent is magnesium sulfate.

The quantity of drying agent to be used in the aldehyde-lowering process of the present invention depends upon many factors, including the drying agent employed, the level of aldehyde and water present in the glycerin, the level and nature of the amine-containing polymeric resin employed, the temperature at which the glycerin is heated and the length of time the heated glycerin is stirred. One skilled in the art will understand how each of these factors affects the reactions that lower the reactive aldehyde levels in the glycerin and will be able to determine, either empirically or through calculation, an adequate quantity of drying agent to be employed in the process. The use of an excess quantity of drying agent in the process is preferred.

Although glycerin derived from any source will benefit from the reactive aldehyde-lowering process described herein, glycerin derived from animals, propylene or plants is preferred. Glycerin derived from propylene or plants is more preferred. Glycerin derived from propylene is most preferred.

Therefore, after selecting a commercial lot of glycerin derived from non-animal sources, preferably freshly manufactured glycerin derived from plants or propylene and more preferably from propylene, the reactive aldehyde content may be determined by an appropriate assay. If the reactive aldehyde content is below the specification limit set for a particular pharmaceutical polypeptide composition, then the glycerin may be incorporated directly into the composition with assurance that the desired level of chemical stability will be achieved.

If the reactive aldehyde content is above the specification limit set for a particular pharmaceutical polypeptide composition, then the reactive aldehyde content of the glycerin may be lowered by treatment by the method described herein. In this manner, a lot of non-animal derived glycerin with a reactive aldehyde content of, for example, 45 ppm or greater may have its reactive aldehyde content lowered to less than 33 ppm prior to its incorporation into a polypeptide composition.

Alternatively, a commercial lot of animal-derived glycerin may be selected and its reactive aldehyde content may be determined prior to its use in preparing a polypeptide composition. Preferably, if measured, the reactive aldehyde content of the glycerin is determined by an assay using a glyceraldehyde standard and, more preferably, the assay is the MBTH Test described herein. If the reactive aldehyde content is below 8 ppm, then the glycerin may be incorporated directly into the composition with assurance that the desired level of chemical stability will be achieved. If the reactive aldehyde content is 8 ppm or greater, then the reactive aldehyde content of the glycerin may be lowered by treatment by the methodology described herein. In this manner, a lot of animal-derived glycerin with a reactive aldehyde content of, for example, 24 ppm may have its reactive aldehyde content lowered, for example, to 2 ppm prior to its incorporation into a polypeptide composition.

The aqueous, parenteral pharmaceutical compositions of the present invention may comprise glycerin derived from non-animal sources to improve its chemical stability. Examples 5–7 of the present specification clearly show improved chemical stability for solution and suspension compositions of pharmaceutical polypeptides comprising glycerin derived from non-animal sources, compared to similar polypeptide compositions comprising glycerin derived from animals.

The aqueous, parenteral pharmaceutical compositions of the present invention may comprise glycerin derived from non-animal sources. If the reactive aldehyde content of the glycerin is measured, the glycerin will preferably have a reactive aldehyde content of less than 33 ppm, to further improve the chemical stability of the polypeptide compositions. Examples 4 and 8 of the present specification clearly show improved chemical stability for solution and suspension compositions of pharmaceutical polypeptides comprising glycerin derived from non-animal sources, and having a reactive aldehyde content of less than 33 ppm compared to similar polypeptide compositions comprising non-animal derived glycerin having a reactive aldehyde content of greater than 33 ppm.

To improve chemical stability, the aqueous, parenteral pharmaceutical compositions of the present invention may alternatively comprise glycerin derived from any source, including glycerin derived from propylene, plants or animals, and having a reactive aldehyde content of less than 8 ppm. Examples 4, 5 and 8 of the present specification clearly show improved chemical stability for solution and suspension compositions of pharmaceutical polypeptides comprising glycerin having a reactive aldehyde content of less than 8 ppm compared to similar polypeptide compositions comprising glycerin having a reactive aldehyde content of 8 ppm or greater.

The present invention is believed to apply to any aqueous polypeptide composition comprising glycerin. Such polypeptide compositions often comprise other components and excipients and are prepared in a manner normally used to prepare such compositions. Without limiting the generality of the present invention, the following compositions, excipients and methods of preparing them will be disclosed to better instruct the reader.

The present invention provides for compositions comprising water, a polypeptide and non-animal derived glycerin or glycerin derived from any source that has a reactive aldehyde content of less than 8 ppm. In particular, the invention provides compositions comprising at least one polypeptide or a pharmaceutically acceptable salt form thereof. The range of polypeptide concentrations that can be used in the invention is from about 1.0 µg/mL to about 100 mg/mL, although lower and higher concentrations are operable, dependent on the route of administration. The polypeptide concentrations are preferably about 5.0 µg/mL to about 20 mg/mL and most preferably about 20 µg/mL to about 10 mg/mL. Based on the dose required, the potency of the polypeptide and the stability of the polypeptide in the formulation, the skilled person will know the proper polypeptide concentrations to incorporate into compositions of the present invention.

Other excipients, such as isotonicity agents in addition to glycerin, preservatives, protamine, buffers, solubilizers, detergents, antioxidants, solution stabilizers and metal cations may be used in the compositions of the present invention according to formulations conventionally used for polypeptides. Yet other excipients are available for use in the polypeptide compositions of the present invention.

The water content of the compositions of the present invention is 500 mg/mL or greater. The glycerin concentration of the polypeptide compositions of the present invention is less than 500 mg/mL.

The pharmaceutical compositions of the present invention may be prepared by a variety of procedures well known in the art. The present invention does not require a prescribed order of addition of components in the composition to be operable. Based on the nature of the peptide, the therapeutic application and the formulation desired, the skilled person will know the proper procedures and order of addition for preparing the compositions of the present invention.

According to the present invention, glycerin derived from plants or propylene, if sufficiently fresh, may be used directly with great confidence to improve the chemical stability of polypeptide compositions compared to the known use of animal-derived glycerin in the same composition. However, the fullest breadth of the present invention will be realized if the reactive aldehyde content of the glycerin to be used in a polypeptide composition is first measured. Preferably, the reactive aldehyde content of the glycerin is determined within two weeks of incorporating it into a polypeptide composition. More preferably, the reactive aldehyde content of the glycerin is measured within three days prior to it incorporation into a composition. Preferably, if measured prior to its use in preparing a polypeptide composition, the reactive aldehyde content of the non-animal derived glycerin is less than 33 ppm. More preferably the glycerin has a reactive aldehyde content of less than 24 ppm. More preferably, the glycerin has a reactive aldehyde content of less than 15 ppm. More preferably, the glycerin has a reactive aldehyde content of less than 8 ppm. Most preferably, the glycerin has a reactive aldehyde content of 3 ppm or lower. Preferably, the assay employed to measure the reactive aldehyde content of the glycerin uses glyceraldehyde as a standard. More preferably, the assay employed to measure the reactive aldehyde content of the glycerin is the MBTH Test described herein.

Alternatively, animal-derived glycerin that may be tested for its reactive aldehyde content in the manner and time frame as described above, may also be used in polypeptide compositions of the present invention with great confidence of improved chemical stability if the glycerin has a reactive aldehyde content of less than 8 ppm.

Therefore, one aspect of the present invention provides aqueous, parenteral pharmaceutical compositions comprising a polypeptide and glycerin in which the glycerin is derived from any source, including glycerin derived from propylene, plants or animals, and in which the glycerin has a reactive aldehyde content of less than 8 ppm. Preferably, the reactive aldehyde content of the glycerin is 3 ppm or lower. Preferably, the assay employed to measure the reactive aldehyde content of the glycerin uses glyceraldehyde as a standard. More preferably, the assay employed to measure the reactive aldehyde content of the glycerin is the MBTH Test described herein.

The aqueous, pharmaceutical polypeptide compositions of the present invention are used as medicaments or to prepare medicaments for the treatment of diseases in mammals. More particularly, when insulin or an analog or derivative of insulin, or GLP-1 or an analog or a derivative of GLP-1 is the polypeptide, the medicament may be used for the treatment of diabetes or hyperglycemia.

The claimed polypeptide compositions may be made available to patients as clear solutions, suspension mixtures, or as dual-vial packages comprising a vial of a lyophilized or dry polypeptide that is reconstituted with diluent from a second vial. Preferred polypeptide compositions are clear solutions and suspension mixtures.

The claimed compositions may be administered to a patient in need thereof by a variety of parenteral delivery methods appreciated by the skilled artisan. Preferred methods include subcutaneous injection, intramuscular injection, intravenous injection or infusion, pulmonary administration, buccal, nasal, intraocular or transdermal delivery, and internal or external pump administration. More preferred delivery methods are subcutaneous and intramuscular injections.

During storage, the claimed compositions are surprisingly more chemically stable than compositions previously known.

Method 1

MBTH Test

"MBTH Solution" is prepared by dissolving about 250 mg of a solid mixture of about 20–25% by weight of 3-methyl-2-benzothiazolinone hydrazone hydrochloride (MBTH) and about 75–80% by weight of sodium chloride in 100 ml total volume of water.

"Ferric Chloride Solution" is prepared by taking about 5.4 gm of a solution comprising about 20–35% by weight of ferric chloride ($FeCl_3$) and about 5% by weight of hydrochloric acid in propylene glycol and adding about 1.5 gm of sulfamic acid. This mixture is then diluted to 100-ml total volume with water.

About 50 mg to about 400 mg samples of glycerin lots to be assayed are accurately weighed in a 15-mL test tube. 1.0 mL of water is added. 4.0 mL of MBTH Solution is then added and the preparation is mixed thoroughly. The solution is then heated for 60±5 seconds in a boiling water bath. After 5 minutes of cooling at ambient temperature, 5.0 mL of Ferric Chloride Solution is added and mixed thoroughly.

After about 30 or more minutes of cooling at ambient temperature the absorbance of the solution at 624 nm is measured on a spectrophotometer.

A blank test solution is prepared as above except the glycerin is deleted. A standard curve is obtained by diluting an aqueous 100 μg/mL solution of glyceraldehyde with additional water to prepare glyceraldehyde standards from about 0.5 μg/ml to about 10 μg/ml. The standard solutions are then treated with the test reagents.

After subtracting out the absorbance of the blank from the absorbance values of the standard and test solutions, the reactive aldehyde level in the glycerin samples is quantified from the glyceraldehyde standard curve. For glycerin samples in which the reactive aldehyde content falls below the 0.5 μg/ml glyceraldehyde standard, the reactive aldehyde content is determined by extrapolating the best fit line obtained with the glyceraldehyde standards. Samples are generally run in triplicate. All water used in this assay is preferably aldehyde-free.

Method 2

10× Glycerin Stress Test (10×-GST)

The 10× Glycerin Stress Test (10×-GST) measures the formation of covalent dimers and polymers in an insulin composition. Glycerin to be tested is added to Humulin® R (U40, Eli Lilly & Co., Indianapolis Ind., USA) to a final concentration of 160 mg/mL of glycerin, i.e., ten times the level of glycerin normally used in this formulation. One aliquot of the resulting formulation is incubated at 30° C. for 7 days, while a second aliquot is stored frozen over the same time period. Then, the high molecular weight protein (HMWP) level of the two aliquots is measured by size exclusion HPLC chromatography under denaturing conditions (e.g., Zorbax GF 250 Special column; mobile phase 65 parts of 0.1M ammonium phosphate buffer at pH 7.5 and 35 parts acetonitrile; detection at 214 nm). The growth of HMWP in the test formulation is the concentration of HMWP in the 30° C. sample minus the concentration of HMWP in the frozen control.

Method 3

Modified 10× Glycerin Stress Test (Mod.10×-GST)

One milliliter of Humulin® N (U40, Eli Lilly & Co., Indianapolis Ind., USA) is spiked with about 160 mg (about 128 μl) of glycerin to be tested. This glycerin level is about ten times the normal level found in commercial products. Another milliliter of Humulin® N U40 is spiked with 128 μL of water. Both samples are stored at 30° C. for 7 days. The high molecular weight protein (HMWP) level of the two samples is then measured by size exclusion HPLC chromatography under denaturing conditions [e.g., Waters column labeled "Protein-Pak 125 insulin assay certified", Waters Corporation (Milford, Mass., USA) part number 20574; mobile phase 65 parts of a 1 mg/mL L-arginine solution, 20 parts of acetonitrile and 15 parts of glacial acetic acid]. The test samples are solubilized by acidification with a small volume of 9.6 N HCl prior to analysis.

The HMWP growth in the sample is calculated as the HMWP level in the 30° C. test sample minus the HMWP level in the water spiked control. Percent growth is reported per 7 day period.

Method 4

HPLC Analysis of Derivatized Aldehydes in Glycerin

A 160 mg sample of a glycerin lot to be tested is derivatized with 1 mL of 0.5 mg/ml of 2-dipheylacetyl-1,3-indandione-1-hydrazone [(DPIH), see Rideout, J. M., et al., Clin. Chim. Acta 161:29–35 (1986) and Swarin, S., et al., J. Liquid Chromatography 6:425–444 (1983)] in acetonitrile in a 3.5 mL glass vial. Ten μL of trifluoroacetic acid is added and the vial is tightly capped and rotated at 20 rpm for 3 hours at ambient temperature. The glycerin is immiscible with the acetonitrile-DPIH reagent solution but the rotation of the vial spreads out the glycerin into a thin layer over the vial's surface, maximizing the bilayer surface contact. The aldehydes and ketones in the glycerin react with DPIH to form azines which are extracted into the acetonitrile-DPIH reagent solution.

The solution is then injected onto a Zorbax Rx C8 HPLC column (Mac-Mod Analytical Inc., Chadds Ford, Pa., USA). The azines are separated by a step gradient made from solution A (0.1% TFA in water) and solution B (0.1% TFA in acetonitrile) stepping from 48% B to 66% B mixtures during the 30 minute run. The derivatives are detected using a spectrophotometer at 290 nm or using a spectrofluorimeter at 425 nm excitation and 525 nm emission. Aldehyde standards are separated, by order of elution; glyceraldehyde, glycolaldehyde, hydroxypropionaldehyde, formaldehyde, acetaldehyde and propionaldehyde.

The following examples are provided merely to further illustrate the invention. The scope of the invention shall not be construed as merely consisting of the following examples.

EXAMPLE 1

Selectivity of Aldehyde Tests

A sample of plant-derived glycerin was spiked with defined levels of aldehydes shown in Table 1. The spiked glycerin samples were then assayed by the MBTH Test described herein (Method 1) and three other tests.

For the "Nash" test, aldehydes in the glycerin were extracted into pH 7.5 phosphate buffer and then derivatized with acetylacetone in the presence of excess ammonium acetate [du Chatinier, et al., Analytical Letters 22:875–883 (1989)]. The colored reaction products were quantified at 415 nm using a spectrophotometer.

For the "Purpald" test, the reagent 4-amino-3-hydrazino-5-mercapto-1,2,4-triazole [Aldrich Chemical Company] was dissolved in 1 N NaOH. This solution was then added to glycerin solutions that had been diluted with water. After aeration, the absorbances of the solutions at 401 nm were determined using a spectrophotometer.

For the European Pharmacopoeia (Ph. Eur.) test, the glycerin solutions were mixed with pararosaniline hydrochloride solution [European Pharmacopoeia 1997, pp. 906–907, Council of Europe, Strasbourg]. After one hour, the absorbance at 550 nm was measured using a spectrophotometer.

The absorbance values for each test were calculated by subtracting the unspiked glycerin sample responses from the spiked glycerin responses for each compound that was added. The absorbances were calculated on a molar basis for each aldehyde and are shown in Table 1. A negative value means the absorbance reading was actually lowered by the addition of the aldehyde.

TABLE 1

Molar Absorbance of Aldehydes Added to Glycerin

|  | Nash Test | MBTH Test | Purpald Test | Ph. Eur. Test |
| --- | --- | --- | --- | --- |
| formaldehyde | 363 | 3567 | 114 | 1090 |
| acetaldehyde | 3 | 2138 | −532 | nd |
| glyceraldehyde | 34 | 1525 | −108 | 85 |
| glycolaldehyde | 10 | 3379 | 3924 | nd | nd = not determined

The Nash method did not generate much absorbance with any of the aldehydes. The Purpald method was highly sensitive to glycolaldehyde but produced no absorbance with glyceraldehyde. The European Pharmacopoeia method generated moderate absorbance with formaldehyde but was relatively insensitive for measuring glyceraldehyde.

This experiment clearly showed that, of the four tests that were compared, the greatest absorbance signal per mole of glyceraldehyde was obtained with the MBTH Test. Glyceraldehyde was shown by HPLC analysis (Method 4) to be the predominant aldehyde found in commercial glycerin lots. In the MBTH Test, large absorbance values were also obtained for formaldehyde and glycolaldehyde, reactive aldehydes shown by HPLC analysis (Method 4) to be present at low levels in commercial glycerin lots. Thus, the MBTH Test is a sensitive method for determining the level of reactive aldehydes in glycerin.

EXAMPLE 2

Correlation of MBTH Test with the Modified 10×-GST Test

The reactive aldehyde content of fresh and aged commercial lots of glycerin was measured by the MBTH Test described herein. Each sample of glycerin was also evaluated using the Modified 10×-GST Test (Method 3). For the combined propylene and plant-derived glycerin samples (n=39, and n=25, respectively) the results displayed in FIG. 1 show a strong, linear correlation ($R^2$=0.90, for the best fit line forced through the origin) between the reactive aldehyde content as measured by the MBTH Test (<100 ppm) and the increased covalent HMWP peaks measured in Humulin® N insulin formulations by the Modified 10×-GST Test. Animal-derived glycerin samples (n=19) also showed a strong, linear correlation between these tests ($R^2$=0.93, data not shown).

EXAMPLE 3

Reactive Aldehyde Content of Aged Commercial Glycerin Lots

Commercial lots of glycerin whose dates of manufacture were known were stored at ambient temperature for 1 to 48 months from their dates of manufacture. For each lot of glycerin, the reactive aldehyde content was measured by the MBTH Test described herein. Data from these lots are shown in Table 2 below.

TABLE 2

Analyses of Reactive Aldehyde in Glycerin Lots Derived from Three Sources

|  | Animal | Plant | Propylene |
| --- | --- | --- | --- |
| Lots Analyzed | 6 | 10 | 36 |
| Age Range (months) | 3–47 | 1–29 | 1.5–48 |
| Average Age (months) | 22.0 | 10.6 | 19.9 |
| Aldehyde Range (ppm) | 24–1069 | 4–43 | 0–169 |
| Aldehyde Average (ppm ± SEM) | 301.5 ± 162.5 | 23.6 ± 4.5 | 25.2 ± 6.2 |
| Aldehyde Average per Average Age (ppm/month) | 13.7 | 2.2 | 1.3 |
| Average of Lot Aldehyde per Month of Age (ppm ± SEM) | 16.5 ± 7.1* | 3.6 ± 1.3* | |

SEM = standard error of the mean
*statistically different, p = 0.003 calculated by Wilcoxon Rank-Sum Test These data clearly show that aged glycerin lots derived from propylene and plants have a lower range of reactive aldehyde levels that those of animal-derived glycerin. These data also show that glycerin lots derived from plant and propylene sources have a much lower average reactive aldehyde content per average age than glycerin lots derived from animal sources.

Data in the last row of Table 2 were obtained by dividing the reactive aldehyde content of each glycerin lot by its age since date of manufacture. These calculations show non-animal derived glycerin has a statistically significant lower level of reactive aldehyde per month of age than animal derived glycerin. A reasonable explanation of these data is that the reactive aldehyde content of animal derived glycerin increased faster over time than the reactive aldehyde content of plant or propylene derived glycerin.

Based on this study we believe that if plant, propylene and animal derived glycerin of equivalent reactive aldehyde content are stored under identical conditions, the reactive aldehyde content of the animal derived glycerin will increase faster over time than the reactive aldehyde content of the plant and propylene derived glycerin.

EXAMPLE 4

Stability of Leptin Formulations

Human leptin analog Asp(72), Asp(100)-Ob, [SEQ. ID. 6 in Beals, J. M., et al., WO 98/28335 published 24 Jun. 1998] was used to prepare formulations containing glycerin at a concentration of 220 mg/ml. Glycerin sample 1 (reactive aldehydes=1 ppm by MBTH Test) was derived from propylene and glycerin sample 2 (reactive aldehydes=85 ppm by MBTH Test) was derived from a plant source. Each formulation contained 15.2 mg/mL of the protein in 10 mM phosphate buffer adjusted to pH 7.8.

A 50 mL volume of each of the sample formulations was prepared concurrently and sterile filtered. Aliquots (3 mL) were then aseptically filled into sterile 5-mL glass vials, stoppered, sealed, and then stored at 5° C. and 25° C. for 3, 7, 10 and 24 days. The solutions were analyzed under dissociating conditions by size exclusion HPLC using a TosoHaas TSK-GEL G3000SW-XL column (TosoHaas, Montgomeryville, Pa., USA) and a mobile phase of 0.1 M sodium phosphate, 0.1 M sodium sulfate and 0.6% sodium dodecyl sulfate at pH 8.5. The eluting polypeptide peaks were detected by ultraviolet absorbance at 214 nm.

In addition to the main protein peak, two earlier-eluting (i.e. larger molecular weight) peaks were observed. One of these was covalent dimer, which represented more than 90% of the earlier-eluting peak area. The other earlier-eluting peak contained covalent protein polymer larger than dimer. On the day of sample preparation, the combined earlier-eluting peak area represented 0.31% to 0.33% of the total chromatogram peak area of the samples, while the dimer peak represented 0.30% to 0.32% of the total chromatogram area.

All samples remained clear and colorless throughout the study. The increases in the high molecular weight protein peaks (combined dimer and larger molecular weight peaks) as a percentage of the total protein are indicated in Table 3 below. As with the starting protein solutions, the earlier-eluting peaks were mostly due to the dimer in all samples.

TABLE 3

Increase in High Molecular Weight Protein Peaks (% of Total Protein)

| Days | Incubation Temperature | Glycerin Sample 1 | Glycerin Sample 2 |
|---|---|---|---|
| 3 | 5° C. | 0.06 | 0.06 |
| 7 | 5° C. | 0.11 | 0.12 |
| 10 | 5° C. | 0.10 | 0.18 |
| 24 | 5° C. | 0.11 | 0.22 |
| 3 | 25° C. | 0.15 | 0.29 |
| 7 | 25° C. | 0.26 | 0.63 |
| 10 | 25° C. | 0.32 | 0.80 |
| 24 | 25° C. | 0.50 | 1.53 |

This experiment showed that for human leptin analog Asp(72)Asp(100)-Ob, formulations containing glycerin with a lower reactive aldehyde content (sample 1) had less formation of higher molecular weight protein impurities during storage at both 5° C. and 25° C. than a comparable composition containing glycerin with a higher reactive aldehyde content (sample 2). After 24 days at 5° C., the level of increased high molecular weight protein in the composition prepared with glycerin having a reactive aldehyde content of 1 ppm (sample 1) was about 50% lower than in the composition prepared with glycerin having a reactive aldehyde content of 85 ppm (sample 2). After 24 days at 25° C., the level of increased high molecular weight protein in the composition prepared with glycerin sample 1 was about 67% lower than in the composition prepared with glycerin sample 2.

EXAMPLE 5

Stability of Insulin and Insulin Analog Formulations

The reactive aldehyde content of three different commercial glycerin lots was quantified by the MBTH Test. Glycerin sample 3 was derived from propylene (1 ppm of reactive aldehyde) and glycerin samples 4 and 5 were animal-derived (45 and 156 ppm of reactive aldehyde, respectively).

Two manufactured formulations of human insulin (soluble Humulin® R and crystalline suspension Humulin® N) and four manufactured formulations of Lys(B28)Pro (B29)-human insulin [soluble Humalog®, crystalline suspension Humalog® NPL, and fixed mixtures thereof termed LisPro Low Mix (25:75, Humalog®:Humalog® NPL, see Roach, P., et al., Diabetes Care 22:1258–1261 (1999)) and LisPro Mid Mix (50:50, Humalog®:Humalog® NPL)], each at 100 unit per mL strength, were spiked with glycerin samples 3, 4 and 5 to a final glycerin concentration of 160 mg/mL.

After 7 days at 30° C., the increase in the percent high molecular weight protein (HMWP) of each formulation was determined as in Method 3. The increase in HMWP levels is shown in Table 4 below.

TABLE 4

Increase in High Molecular Weight Protein Peaks After 7 Days at 30° C. (% of Total Protein)

| Formulation | Glycerin Sample 3 | Glycerin Sample 4 | Glycerin Sample 5 |
|---|---|---|---|
| Humulin ® N | 0.04 | 1.85 | 5.18 |
| Humalog ® NPL | 0.11 | 1.69 | 4.61 |
| LisPro Low Mix | 0.17 | 1.38 | 4.27 |
| LisPro Mid Mix | 0.05 | 1.05 | 3.78 |
| Humulin ® R | 0.05 | 0.78 | 3.21 |
| Humalog ® | 0.05 | 0.46 | 2.68 |

The results of this experiment clearly show that the use of non-animal derived glycerin provides solutions, suspensions and mixed solution/suspensions of polypeptides with improved chemical stability compared to similar compositions prepared with animal derived glycerin. After 7 days at 30° C., the levels of increased high molecular weight protein in the compositions prepared with propylene derived glycerin (sample 3) ranged from about 87% lower for LisPro Low Mix (compared to animal derived glycerin sample 4) to about 99% lower for Humulin® N (compared to animal derived glycerin sample 5).

EXAMPLE 6

Preparation of Lys(B28)Pro(B29)-Human Insulin Suspensions

Compositions corresponding to U100 strength Lys(B28) Pro(B29)-human insulin analog suspensions (Humalog® NPL, Eli Lilly & Co., Indianapolis, Ind., USA) were prepared employing four commercial lots of glycerin that were not further purified.

First, the reactive aldehyde content of three of the glycerin lots was determined by the MBTH Test as described in Method 1. The glycerin lots were also evaluated using the 10× Glycerin Stress Test (Method 2) and the Modified 10× Glycerin Stress Test (Method 3). The results of these analyses are reported in Table 5 below.

TABLE 5

Analyses of Glycerin Lots Used to Prepare
Lys (B28) Pro (B29)-Human Insulin Suspensions

| Glycerin Sample | Source | MBTH Test | 10X-GST Test | Mod. 10X-GST Test |
|---|---|---|---|---|
| 6 | Propylene | 1 | 0.13 | 0.13 |
| 7 | Propylene | 2 | 0.22 | 0.09 |
| 8 | Propylene | 1 | 0.01 | 0.17 |
| 9 | Animal | nd | nd | nd | nd = not determined

To prepare the Lys(B28)Pro(B29)-human insulin formulations, several intermediate solutions were prepared.

A "preservative stock solution" containing 3.52 mg/mL m-cresol and 1.43 mg/mL phenol (calculated at 89% by weight) was prepared in deionized water.

"Glycerin stock solutions" for each sample of glycerin were prepared at 160 mg/mL in water.

A "zinc stock solution" was prepared by acidifying a solution of zinc oxide with 10% HCl.

"Preservative-glycerin-zinc solutions" were prepared by combining appropriate volumes of the "preservative stock solution", the "glycerin stock solutions" and the "zinc stock solution" sufficient to result in a solution containing 1.76 mg/mL m-cresol, 0.715 mg/mL phenol, 16 mg/mL glycerin and a zinc concentration that, when combined with the zinc present in the bulk Lys(B28)Pro(B29)-human insulin material, totaled 25 µg/mL. At this time the "preservative-glycerin-zinc" solutions were about pH 4.7.

Quantities of Lys(B28)Pro(B29)-human insulin (bulk zinc crystals) were then added to the preservative-glycerin-zinc solutions at a level sufficient to achieve a concentration of 200 units (U) per mL, or about 7.0 mg/mL in the "U200 Lys(B28)Pro(B29)-human insulin solutions" described below. Dissolution of Lys(B28)Pro(B29)-human insulin was effected at room temperature by lowering the pH to about 2.8 by the addition of small aliquots of 10% HCl. After the solutions were clarified, the pH of each was readjusted to about 7.3 by the addition of small aliquots of 10% NaOH. Volumes of a dibasic sodium phosphate heptahydrate solution at 75.6 mg/mL in deionized water were added at levels sufficient to result in a concentration of 3.78 mg/mL dibasic sodium phosphate heptahydrate in this solution. After stirring to complete dissolution of all material in the solution, 10% NaOH was added to adjust each of the four Lys(B28) Pro(B29)-human insulin solutions to about pH 7.4. Deionized water was added to result in 200 U/mL solutions of Lys(B28)Pro(B29)-human insulin, which were then filtered through 0.22 micron Sterivex GV filters (Millipore Products Division, Bedford, Mass., USA). These four solutions are termed "U200 Lys(B28)Pro(B29)-human insulin solutions".

"Protamine stock solution" was prepared by dissolving solid protamine sulfate (Chum salmon) in "preservative stock solution" to achieve a concentration equivalent to 0.6 mg/mL of protamine free base in the final "protamine-preservative-glycerin solutions" described below. After stirring for 45 minutes, a volume of dibasic sodium phosphate heptahydrate solution at 75.6 mg/mL in deionized water was added to result in a concentration of 3.78 mg/mL of dibasic sodium phosphate heptahydrate in the final "protamine-preservative-glycerin solution". The solution was then adjusted to pH 7.4 by addition of small aliquots of 10% hydrochloric acid. Volumes of the 160 mg/mL "glycerin stock solutions" were then added to result in solutions containing 16 mg/mL of glycerin in each solution. Deionized water was added to adjust the final volume and the four "protamine-preservative-glycerin" solutions were filtered through 0.22 micron Sterivex GV filters.

After equilibrating each of the four U200 Lys(B28)Pro (B29)-human insulin solutions and each of the four protamine-preservative-glycerin solutions at 15° C., equal volumes of each solution were combined and incubated for 61 hours at 15° C.

Each mL of the resulting four suspension formulations prepared in this experiment contained approximately: 3.5 mg Lys(B28)Pro(B29)-human insulin, 3.78 mg dibasic sodium phosphate heptahydrate, 16 mg glycerin, 1.76 mg m-cresol, 0.715 mg phenol, 25 µg zinc and 0.3 mg protamine.

EXAMPLE 7

Stability of Lys(B28)Pro(B29)-Human Insulin Suspensions

The four suspension formulations of Lys(B28)Pro(B29)-human insulin prepared with different lots of glycerin as described in Example 6 were incubated for up to 12 weeks at 30° C. At various times, the high molecular weight protein (HMWP) level in the samples, as a percent of total protein, was measured by the size exclusion HPLC chromatography method described for the Modified 10×-GST Test (Method 3). The results of the stability test are shown in Table 6 below.

TABLE 6

HMWP Levels in Lys(B28)Pro(B29)Human Insulin
Suspensions Prepared with Various Glycerin Lots

| Weeks at 30° C. | Glycerin Sample 6 | Glycerin Sample 7 | Glycerin Sample 8 | Glycerin Sample 9 |
|---|---|---|---|---|
| 0 | 0.24 | 0.20 | 0.20 | 0.23 |
| 1 | 0.41 | 0.39 | 0.40 | 0.64 |
| 2 | 0.55 | 0.51 | 0.54 | 0.92 |
| 4 | 0.75 | 0.71 | 0.77 | 1.43 |
| 8 | 1.24 | 1.21 | 1.28 | 2.15 |
| 12 | 2.00 | 1.95 | 2.02 | 3.16 |

The results of this experiment clearly show that glycerin derived from propylene improved the chemical stability of Lys(B28)Pro(B29)-human insulin suspension formulations compared to suspensions prepared with animal-derived glycerin. After 12 weeks at 30° C., the level of increased high molecular weight protein in the suspension formulations prepared with glycerin derived from propylene (samples 6 to 8) was, on average, about 39% lower than the level of increased HMWP in the formulation prepared with glycerin derived from animals (sample 9).

EXAMPLE 8

Lowering the Level of Reactive Aldehydes in Glycerin

Glycerin (3.0 gm) from a lot derived from propylene was placed into each of five beakers containing stir bars. Five beakers were similarly prepared using a lot of plant-derived glycerin. About 50 mg of solid anhydrous magnesium sulfate ($MgSO_4$) was added to four beakers in each set. To three beakers in each set to which the magnesium sulfate was added, was added a weighed amount of one of the following polymeric resins from Advanced ChemTech Inc. (Louisville, Ky., USA): Resin A, 0.1 gm of Tris (2-aminoethyl) amine resin (0.7 mmol/gm, 100–200 mesh); Resin B, 0.2 gm TantaGel® S NH2 resin (0.3 mmol/gm, 90 um); Resin C, 0.1 gm aminomethyl polystyrene resin (0.7 mmol/gm, 100–200 mesh).

All ten beakers were placed on a stir plate in a glovebag under a nitrogen atmosphere and heated to about 60° C. After stirring for 24 hours, the samples were plug-filtered through a cellulose membrane and analyzed for their reactive aldehyde content (ppm) by the MBTH Test described in Method 1. Several of the glycerin samples were also evaluated by the Modified 10x-GST Test (Method 3). The results of this experiment are reported in Table 7 below.

TABLE 7

Results of Treatment of Glycerin Samples with Polymeric Amine Resins

| Sample | Glycerin Source | $MgSO_4$ | Resin | MBTH Test | Mod. 10X-GST Test |
|---|---|---|---|---|---|
| 1 | Propylene | No | None | 21 | 1.84 |
| 2 | Propylene | Yes | None | 25 | 1.58 |
| 3 | Propylene | Yes | A | 2 | nd |
| 4 | Propylene | Yes | B | 1 | nd |
| 5 | Propylene | Yes | C | 1 | −0.27 |
| 6 | Plant | No | None | 36 | 4.68 |
| 7 | Plant | Yes | None | 45 | 3.65 |
| 8 | Plant | Yes | A | 10 | nd |
| 9 | Plant | Yes | B | 3 | nd |
| 10 | Plant | Yes | C | 1 | −0.03 | nd = not determined

These data clearly show that the purification methods employed greatly reduced the concentration of reactive aldehydes in commercial glycerin lots. In insulin suspensions examined in the Modified 10x-GST Test, the glycerin lots purified with aminomethyl polystyrene (Resin C) led to no increase in the HMWP peaks while the unpurified glycerin lots led to significantly increased levels of the HMWP peaks.

EXAMPLE 9

Human Insulin Solution

Recombinant human insulin (35 mg) is dissolved in about 5 ml of 0.01 N HCl. Zinc oxide solution (1 mL, 0.17 mg/mL zinc as zinc oxide dissolved in 0.1 N HCl) is added, followed by 25 mg of m-cresol. Then, 160 mg of freshly manufactured glycerin derived from propylene is added. The solution is adjusted to about pH 7.4 with 1 N NaOH and diluted to about 10 mL total volume with water. Each mL of this polypeptide composition contains about 3.5 mg human insulin, about 16 mg glycerin, about 2.5 mg m-cresol and about 0.017 mg zinc.

EXAMPLE 10

Human Insulin Solution

Recombinant human insulin (35 mg) is dissolved in about 5 ml of 0.01 N HCl. Zinc oxide solution (1 mL, 0.17 mg/mL zinc as zinc oxide dissolved in 0.1 N HCl) is added, followed by 16 mg of m-cresol, 6.5 mg phenol and 1 mL of 140 mM sodium phosphate buffer in water. Then, 160 mg of freshly manufactured glycerin derived from propylene is added. The solution is adjusted to about pH 7.4 with 1 N NaOH and diluted to about 10 mL total volume with water. Each mL of this polypeptide composition contains about 3.5 mg human insulin, about 16 mg glycerin, 14 mM sodium phosphate, about 1.6 mg m-cresol, about 0.65 mg phenol and about 0.017 mg zinc.

EXAMPLE 11

Human Insulin Suspension

A suspension of human insulin-protamine crystals is prepared by first dissolving 35 mg of recombinant human insulin in 5 ml of 0.01 N HCl, followed by adding 16 mg m-cresol and 6.5 mg phenol. Then, 1 ml of a 160 mg/mL aqueous solution of glycerin derived from propylene, 1 mL of a zinc oxide (0.25 mg/ml zinc) solution in 0.1 N HCl, and 2.7 mg protamine (on a free-base basis) are added, followed by dilution to about 9 mL total volume with water. A solution (1 ml) of a 38 mg/mL dibasic sodium phosphate heptahydrate solution is then added, resulting in a pH of about 8. The resulting solution is adjusted to pH 7.4 and crystallization proceeds for about 24 hours at about 19° C. Each mL of this suspension contains about 3.5 mg human insulin, about 16 mg glycerin, about 0.27 mg protamine (on a free-base basis), about 0.025 mg zinc, about 1.6 mg m-cresol, about 0.65 mg phenol and about 3.8 mg dibasic sodium phosphate.

EXAMPLE 12

Human Insulin 70/30 Mixture

A mixture comprising 70 parts of the suspension described in Example 11 is combined with 30 parts of the human insulin solution described in Example 10. Both of these preparations employ glycerin derived from propylene.

EXAMPLE 13

Human Insulin 50/50 Mixture

A mixture comprising 50 parts of the suspension described in Example 11 is combined with 50 parts of the human insulin solution described in Example 10. Both of these preparations employ glycerin derived from propylene.

EXAMPLE 14

Human Insulin 30/70 Mixture

A mixture comprising 30 parts of the suspension described in Example 11 is combined with 70 parts of the human insulin solution described in Example 10. Both of these preparations employ glycerin derived from propylene.

EXAMPLE 15

Lys(B28)Pro(B29)-Human Insulin Solution

Recombinant Lys(B28)Pro(B29)-human insulin (35 mg) is dissolved in about 5 ml of 0.01 N HCl. A 1 mL solution of zinc oxide (0.2 mg/ml zinc) dissolved in 0.1 N HCl is added, followed by 31.5 mg of m-cresol and 1 mL of a 70 mM phosphate buffer solution in water. Then 160 mg of glycerin derived from propylene is added. The solution is adjusted to about pH 7.4 with 1 N NaOH and diluted to about 10 mL total volume with water. Each mL of this polypeptide composition contains about 3.5 mg Lys(B28) Pro(B29)-human insulin, about 16 mg glycerin, 7 mM sodium phosphate, about 3.15 mg m-cresol and about 0.02 mg zinc.

EXAMPLE 16

Lys(B28)Pro(B29)-Human Insulin Solution

Recombinant Lys(B28)Pro(B29)-human insulin (35 mg) is dissolved in about 5 ml of 0.01 N HCl. A 1 mL solution of zinc oxide (0.2 mg/ml zinc) dissolved in 0.1 N HCl is added, followed by 16 mg of m-cresol, 6.5 mg phenol and 1 mL of a 140 mM phosphate buffer solution in water. Then 160 mg of glycerin derived from propylene is added. The solution is adjusted to about pH 7.4 with 1 N NaOH and diluted to about 10 mL total volume with water. Each mL of this polypeptide composition contains about 3.5 mg Lys (B28)Pro(B29)-human insulin, about 16 mg glycerin, 14 mM sodium phosphate, about 1.6 mg m-cresol, about 0.65 mg phenol and about 0.02 mg zinc.

EXAMPLE 17

Lys(B28)Pro(B29)-Human Insulin Suspension

A suspension of NPH-like crystals of Lys(B28)Pro(B29)-human insulin is prepared using glycerin derived from propylene using the procedure described in Example 6.

EXAMPLE 18

Lys(B28)Pro(B29)-Human Insulin 75/25 Mixture

A mixture comprising 75 parts of the Lys(B28)Pro(B29)-human insulin suspension described in Example 17 is combined with 25 parts of the Lys(B28)Pro(B29)-human insulin solution described in Example 16. Each of these preparations employs glycerin derived from propylene.

EXAMPLE 19

Lys(B28)Pro(B29)-Human Insulin 50/50 Mixture

A mixture comprising 50 parts of the Lys(B28)Pro(B29)-human insulin suspension described in Example 17 is combined with 50 parts of the Lys(B28)Pro(B29)-human insulin solution described in Example 16. Each of these preparations employs glycerin derived from propylene.

EXAMPLE 20

Lys(B28)Pro(329)-Human Insulin 25/75 Mixture

A mixture comprising 25 parts of the Lys(B28)Pro(B29)-human insulin suspension described in Example 17 is combined with 75 parts of the Lys(B28)Pro(B29)-human insulin solution described in Example 16. Each of these preparations employs glycerin derived from propylene.

EXAMPLE 21

Asp(B28)-Human Insulin Solution

Recombinant Asp(B28)-human insulin (35 mg) is dissolved in about 5 ml of 0.01 N HCl. A 1 mL solution of zinc oxide (0.2 mg/ml zinc) dissolved in 0.1 N HCl is added, followed by 17 mg m-cresol and 15 mg phenol. Then 160 mg of glycerin derived from propylene is added, followed by 1 mL of a 70 mM phosphate buffer solution in water. The solution is then adjusted to about pH 7.4 with 1 N NaOH and diluted to about 10 mL total volume with water. Each mL of this polypeptide composition contains about 3.5 mg Asp (B28)-human insulin, about 16 mg glycerin, about 7 mM phosphate, about 1.7 mg m-cresol, about 1.5 mg phenol and about 0.02 mg zinc.

EXAMPLE 22

Asp(B28)-Human Insulin 70/30 Mixture

A solution of Asp(B28)-human insulin is prepared by dissolving 76.5 mg Asp(B28)-human insulin in water containing about 0.32 mL of 0.2 N HCl and adding about 0.16 mL of a 0.4 mg/mL zinc chloride solution. Then, protamine sulfate (equivalent to about 4.5 mg of protamine free base) in water is added, followed by a mixture consisting of 17.2 mg m-cresol, 15 mg phenol and 160 mg glycerin derived from propylene, all dissolved in water. The resulting solution, which is about pH 2.7, is diluted to 10 mL with water and equilibrated to about 30° C. To this solution is added 10 mL of a solution containing 17.2 mg m-cresol, 15 mg phenol, 25 mg disodium phosphate dihydrate and 160 mg of glycerin derived from propylene at pH 9 and equilibrated to about 30° C. After 2 days at about 30° C., crystallization is complete, resulting in a suspension mixture with about 70% of the Asp(B28)-human insulin residing in the insoluble NPH-like crystals and 30% in solution.

EXAMPLE 23

Asp(B28)-Human Insulin 50/50 Mixture

A solution of Asp(B28)-human insulin is prepared by dissolving 76.5 mg Asp(B28)-human insulin in water containing about 0.32 mL of 0.2 N HCl and adding about 0.16 mL of a 0.4 mg/mL zinc chloride solution. Then, protamine sulfate (equivalent to about 3.2 mg of protamine free base) in water is added, followed by a mixture consisting of 17.2 mg m-cresol, 15 mg phenol and 160 mg glycerin derived from propylene, all dissolved in water. The resulting solution, which is about pH 2.7, is diluted to 10 mL with water and equilibrated to about 30° C. To this solution is added 10 mL of a solution containing 17.2 mg m-cresol, 15 mg phenol, 25 mg disodium phosphate dihydrate and 160 mg of glycerin derived from propylene at pH 9 and equilibrated to about 30° C. After 2 days at about 30° C., crystallization is complete, resulting in a suspension mixture with about 50% of the Asp(B28)-human insulin residing in the insoluble NPH-like crystals and 50% in solution.

EXAMPLE 24

Asp(B28)-Human Insulin 30/70 Mixture

A solution of Asp(B28)-human insulin is prepared by dissolving 76.5 mg Asp(B28)-human insulin in water containing about 0.32 mL of 0.2 N HCl and adding about 0.16 mL of a 0.4 mg/mL zinc chloride solution. Then, protamine sulfate (equivalent to about 2.0 mg of protamine free base) in water is added, followed by a mixture consisting of 17.2 mg m-cresol, 15 mg phenol and 160 mg glycerin derived from propylene, all dissolved in water. The resulting solution, which is about pH 2.7, is diluted to 10 mL with water and equilibrated to about 30° C. To this solution is added 10 mL of a solution containing 17.2 mg m-cresol, 15 mg phenol, 25 mg disodium phosphate dihydrate and 160 mg of glycerin derived from propylene at pH 9 and equilibrated to about 30° C. After 2 days at about 30° C., crystallization is complete, resulting in a suspension mixture with about 30% of the Asp(B28)-human insulin residing in the insoluble NPH-like crystals and 70% in solution.

EXAMPLE 25

Myristoyl-ϵ-Lys(B29)-des(B30)-Human Insulin Solution

Insulin analog derivative myristoyl-ϵ-Lys(B29)-des(B30)-human insulin (37 mg) is dissolved in about 5 ml of 0.01 N HCl. A 1 mL solution of zinc oxide (0.17 mg/ml zinc) dissolved in 0.1 N HCl is added, followed by 32 mg of m-cresol, 1 ml of a 70 mM phosphate buffer solution in water, and then 160 mg of glycerin derived from propylene. The solution is adjusted to about pH 7.9 and diluted to about 10 mL total volume with water. Each mL of this polypeptide composition contains about 3.7 mg myristoyl-ϵ-Lys(B29)-des(B30)-human insulin, about 16 mg glycerin, 7 mM sodium phosphate, about 3.2 mg m-cresol and about 0.017 mg zinc.

EXAMPLE 26

Gly(A21)Arg(B21)Arg(B32)-Human Insulin Solution

Insulin analog Gly(A21)Arg(B31)Arg(B32)-human insulin (37 mg) is dissolved in about 5 ml of 0.01 N HCl. A 1 mL solution of zinc oxide (0.80 mg/ml zinc) dissolved in 0.1 N HCl is added. Benzyl alcohol (100 mg) is added, followed by 188 mg of glycerin derived from plants. The solution is adjusted to about pH 4.0 and diluted to about 10 mL total volume with water. Each mL of this polypeptide composition contains about 3.7 mg Gly(A21)Arg(B31)Arg(B32)-human insulin, about 16 mg glycerin, about 0.08 mg zinc and 10 mg of benzyl alcohol.

EXAMPLE 27

Gly(8)-GLP-1 Solution

Gly(8)-GLP-1 (10 mg) is dissolved in about 5 ml of 0.01 N NaOH. Then, m-cresol (20 mg) is added, followed by 160 mg of glycerin derived from animals that has a reactive aldehyde content of 2 ppm as measured by the MBTH Test described herein. The solution is adjusted to pH 8.0 and diluted to 10 mL total volume with water. Each mL of this polypeptide composition contains about 1 mg of Gly(8)-GLP-1, about 16 mg glycerin and 2 mg of m-cresol.

EXAMPLE 28

Human Leptin Solution

Recombinant human leptin (10 mg) is dissolved in about 5 ml of 0.01 N NaOH. Then, m-cresol (30 mg) is added, followed by 160 mg of glycerin derived from plants and 1 mL of a 70 mM phosphate buffer solution in water. The solution is adjusted to pH 8.0 and diluted to 10 mL total volume with water. Each mL of this polypeptide composition contains about 1 mg of human leptin, about 16 mg glycerin, 7 mM sodium phosphate and 3 mg of m-cresol.

EXAMPLE 29

Human FSH Solution

Recombinant human FSH (5 mg) is dissolved in 10 mM sodium phosphate pH 7.4 solution. To this solution is added 30 mg of m-cresol followed by 160 mg of glycerin derived from propylene. The solution is diluted to 10 mL total volume with 10 mm sodium phosphate pH 7.4 solution. Each mL of this polypeptide composition contains 0.5 mg FSH, about 10 mM sodium phosphate, 3 mg m-cresol and 16 mg glycerin.

EXAMPLE 30

Gly(A21)Arg(B21)Arg(B32)-Human Insulin Solution

Insulin analog Gly(A21)Arg(B31)Arg(B32)-human insulin (36 mg) is dissolved in about 5 ml of 0.01 N HCl. A 1 mL solution of zinc oxide (0.30 mg/ml zinc) dissolved in 0.1 N HCl is added. Then, m-cresol (27 mg) is added, followed by 200 mg of an 85% glycerin-15% water solution in which the glycerin is derived from propylene. The solution is adjusted to pH 4.0 and diluted to about 10 mL total volume with water. Each mL of this aqueous polypeptide composition contains about 3.6 mg Gly(A21)Arg(B31)Arg(B32)-human insulin, about 17 mg of glycerin derived from propylene, about 0.03 mg zinc and about 2.7 mg of m-cresol.

EXAMPLE 31

Asp(B28)-Human Insulin Solution

Recombinant Asp(B28)-human insulin (35 mg) is dissolved in about 5 ml of 0.01 N HCl. A 1 mL solution of zinc oxide (0.2 mg/ml zinc) dissolved in 0.1 N HCl is added, followed by 17 mg m-cresol and 15 mg phenol. Then 160 mg of glycerin derived from propylene is added, followed by 1 mL of a 70 mM phosphate buffer solution containing 5.8 mg/ml sodium chloride (NaCl) in water. The solution is then adjusted to about pH 7.4 with 1 N NaOH and diluted to about 10 mL total volume with water. Each mL of this polypeptide composition contains about 3.5 mg Asp(B28)-human insulin, about 16 mg of glycerin, about 7 mM phosphate, about 1.7 mg m-cresol, about 1.5 mg phenol, about 0.58 mg NaCl and about 0.02 mg zinc.

EXAMPLE 32

Arg(34), N-ε-(γ-Glu(N-α-hexadecanoyl))-Lys(26)-GLP-1(7-37)OH Solution

Arg(34), N-ε-(γ-Glu(N-α-hexadecanoyl))-Lys(26)-GLP-1(7-37)OH (10 mg) is dissolved in about 5 ml of 0.01 N NaOH. Then, m-cresol (20 mg) is added, followed by 160 mg of glycerin derived from propylene. The solution is adjusted to pH 8.0 and diluted to 10 mL total volume with water. Each mL of this polypeptide composition contains about 1 mg of Arg(34), N-ε-(γ-Glu(N-α-hexadecanoyl))-Lys(26)-GLP-1(7-37)OH, about 16 mg of glycerin and about 2 mg of m-cresol.

EXAMPLE 33

Exendin-4 Composition

Exendin-4 (1 mg) is added to 5 ml of a pH 4.5 solution containing 5 mg/mL sodium acetate. Then, m-cresol (27 mg) is added, followed by 160 mg of glycerin derived from propylene. The resulting composition is adjusted, if necessary, to pH 4.5 and diluted to 10 mL total volume with water. Each mL of this polypeptide composition contains about 0.1 mg of exendin-4, about 2.5 mg of sodium acetate, about 16 mg of glycerin and about 2.7 mg of m-cresol.

EXAMPLE 34

Lys(B3)Ile(B28)-Human Insulin Solution

Recombinant Lys(B3)Ile(B28)-human insulin (35 mg) is dissolved in about 5 ml of 0.01 N HCl. A 1 mL solution of zinc oxide (0.2 mg/ml zinc) dissolved in 0.1 N HCl is added, followed by 31.5 mg of m-cresol and 1 mL of a 70 mM phosphate buffer solution in water. Then 160 mg of glycerin derived from propylene is added. The solution is adjusted to about pH 7.8 with 1 N NaOH and diluted to about 10 mL total volume with water. Each mL of this polypeptide composition contains about 3.5 mg Lys(B3)Ile(B28)-human insulin, about 16 mg glycerin, about 7 mM sodium phosphate, about 3.15 mg m-cresol and about 0.02 mg zinc.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. An aqueous, parenteral pharmaceutical composition for improving stability of a polypeptide comprising the polypeptide and glycerin, wherein the glycerin comprises propane-1,2,3-triol and reactive aldehyde impurities, the glycerin is derived from a non-animal source, the concentration of propane-1,2,3-triol is less than 500 mg/mL, and the content of reactive aldehyde impurities is less than 33 ppm.

2. The composition according to claim 1, wherein the composition is a solution.

3. The composition according to claim 1, wherein the composition is a suspension.

4. The composition according to claim 1, wherein the glycerin concentration in the pharmaceutical composition is about 1 mg/mL to about 300 mg/mL.

5. The composition according to claim 4, wherein the glycerin concentration is about 3 mg/mL to about 100 mg/mL.

6. The composition according to claim 5, wherein the glycerin concentration is about 10 mg/mL to about 30 mg/mL.

7. The composition according to claim 6, wherein the glycerin concentration is about 15 mg/mL to about 18 mg/mL.

8. The composition according to claim 1, wherein the glycerin is derived from plants or propylene.

9. The composition according to claim 8, wherein the glycerin is derived from propylene.

10. The composition according to claim 1, wherein the glycerin has a reactive aldehyde content of less than 24 ppm.

11. The composition according to claim 10, wherein the glycerin has a reactive aldehyde content of less than 15 ppm.

12. The composition according to claim 11, wherein the glycerin has a reactive aldehyde content of less than 8 ppm.

13. The composition according to claim 12, wherein the glycerin has a reactive aldehyde content of 3 ppm or lower.

14. The composition according to claim 1, wherein the polypeptide is FSH, a FSH analog having deletion of one, two, three or more C-terminal residues of the FSH beta subunit, PTH, a PTH(1–38) fragment, a PTH(1–34) fragment, HGH, GLP-1 or an analog or derivative thereof, human insulin or an analog or derivative thereof, or a derivative of a human insulin analog.

15. The composition according to claim 14, wherein the polypeptide is human insulin or an analog or derivative thereof, or a derivative of a human insulin analog.

16. The composition according to claim 15, wherein the polypeptide is human insulin.

17. The composition according to claim 15, wherein the polypeptide is an analog of human insulin.

18. The composition according to claim 17, wherein the analog is Lys(B28)-Pro(B29)-human insulin.

19. The composition according to claim 17, wherein the analog is Asp(B28)-human insulin.

20. The composition according to claim 17, wherein the analog is Gly(A21)Arg(B31)Arg(B32)-human insulin.

21. The composition according to claim 15, wherein the polypeptide is a derivative of human insulin or a derivative of a human insulin analog.

22. The composition according to claim 21, wherein the derivative of a human insulin analog is myristoyl-ε-Lys(B29)-des(B30)-human insulin.

23. The composition according to claim 21, wherein the derivative of human insulin is palmitoyl-ε-Lys(B29)-human insulin.

* * * * *